United States Patent
Greening, II et al.

(10) Patent No.: US 9,456,935 B2
(45) Date of Patent: Oct. 4, 2016

(54) ABSORBENT ARTICLES COMPRISING RAISED BARRIERS

(71) Applicant: The Procter & Gamble Company, Cincinnati, OH (US)

(72) Inventors: Nelson Edward Greening, II, Cincinnati, OH (US); Marie B. O'Reilly, Cincinnati, OH (US); Barry Robert Feist, Madeira, OH (US); Lisa J. Goodlander, Okeana, OH (US); Rachael Eden Walther, Union, KY (US); Tina Maria Glahn, Cincinnati, OH (US); Kathleen Quinlan Ames-Ooten, Cincinnati, OH (US); Sue Ann Mills, Cincinnati, OH (US); Vera Hille, London (DE); Nicolette Johanna Birgitta Maria Vanderklaauw, Cincinnati, OH (US); Donald Carroll Roe, West Chester, OH (US); Sharon Irene Grenberg, Fairfield, OH (US); Alfred Grant Edwards, Okeana, OH (US); Bruce J. Bader, Cincinnati, OH (US); Robert Christopher Frost, Portland, OR (US)

(73) Assignee: The Procter & Gamble Company, Cincinnati, OH (US)

( * ) Notice: Subject to any disclaimer, the term of this patent is extended or adjusted under 35 U.S.C. 154(b) by 405 days.

(21) Appl. No.: 13/718,041

(22) Filed: Dec. 18, 2012

(65) Prior Publication Data
US 2014/0171898 A1    Jun. 19, 2014

(51) Int. Cl.
| A61F 13/15 | (2006.01) |
|---|---|
| A61F 13/20 | (2006.01) |
| A61F 13/494 | (2006.01) |
| A61F 13/505 | (2006.01) |
| A61F 13/513 | (2006.01) |

(52) U.S. Cl.
CPC ....... *A61F 13/49473* (2013.01); *A61F 13/505* (2013.01); *A61F 13/51394* (2013.01); *A61F 2013/15365* (2013.01); *A61F 2013/15373* (2013.01)

(58) Field of Classification Search
CPC ................ A61F 2013/49493; A61F 13/49473
See application file for complete search history.

(56) References Cited

U.S. PATENT DOCUMENTS

| | | |
|---|---|---|
| 5,462,541 A | 10/1995 | Bruemmer |
| 5,766,411 A | 6/1998 | Wilson |
| 5,776,122 A | 7/1998 | Faulks |
| 6,133,501 A | 10/2000 | Hallock |
| 6,450,998 B1 | 9/2002 | Otsubo |
| 6,458,114 B1 | 10/2002 | Mishima |
| 6,699,228 B1 * | 3/2004 | Chmielewski ........ A61F 13/495 604/368 |
| 6,895,603 B2 | 5/2005 | Coates |
| 7,918,840 B2 * | 4/2011 | Corneliusson ........... 604/385.28 |
| 2002/0052587 A1 | 5/2002 | Magnusson |
| 2002/0055726 A1 | 5/2002 | Costa |
| 2003/0114805 A1 | 6/2003 | Rainville-Lonn |
| 2003/0120233 A1 | 6/2003 | Ohshima |
| 2003/0139724 A1 * | 7/2003 | Ragnarson et al. ..... 604/385.08 |
| 2004/0116883 A1 | 6/2004 | Krautkramer |
| 2004/0138637 A1 | 7/2004 | Mishima |
| 2004/0220541 A1 | 11/2004 | Suzuki |
| 2005/0148983 A1 * | 7/2005 | Doverbo ........... A61F 13/15699 604/385.101 |
| 2006/0069366 A1 | 3/2006 | Cole |
| 2006/0287635 A1 | 12/2006 | Angel, Jr. |
| 2010/0137825 A1 * | 6/2010 | Een et al. ................. 604/385.23 |
| 2013/0090619 A1 | 4/2013 | Carbonari et al. |

* cited by examiner

*Primary Examiner* — Michele M Kidwell
(74) *Attorney, Agent, or Firm* — Christian M. Best

(57) ABSTRACT

An absorbent article comprising a raised barrier is provided. The raised barrier extends into a front waist region, a crotch region, and a back waist region of the absorbent article.

19 Claims, 17 Drawing Sheets

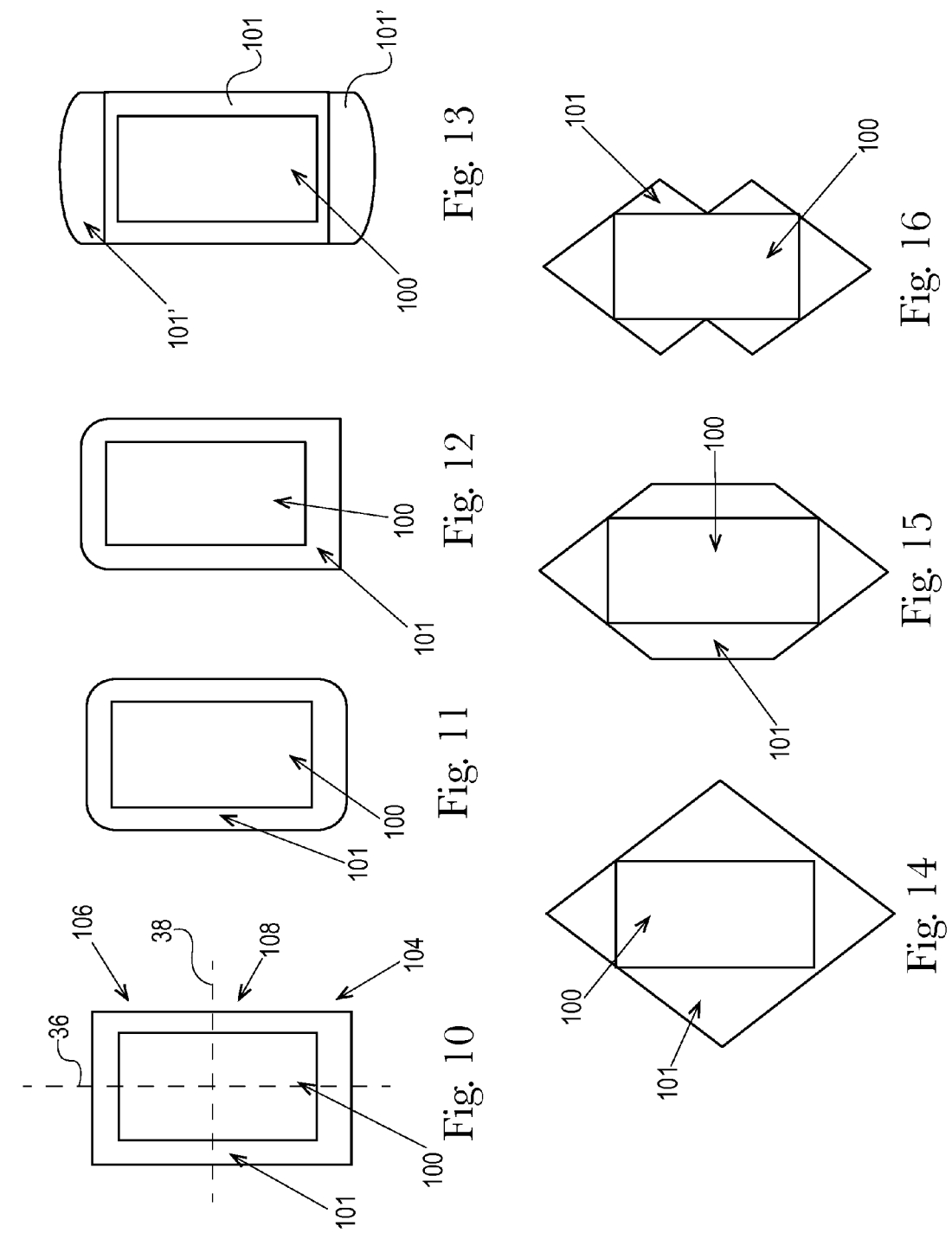

ABSORBENT ARTICLES COMPRISING RAISED BARRIERS

FIELD

The present disclosure relates to absorbent articles comprising absorbent bodies and raised barriers.

BACKGROUND

In absorbent articles, often the rate of urination or runny bowel movement (BM) discharge exceeds the rate of absorption of the absorbent portions of the articles. Features of the absorbent articles, such as barrier cuffs, waistbands, and other elements are designed to contain the free fluid for an amount of time until it can be absorbed by the absorbent portions of the articles. However, there is still a need for additional features to prevent leakage and better contain free fluid in absorbent articles.

SUMMARY

The present disclosure is directed generally to absorbent articles having a raised barrier that fully, or at least partially, surrounds an absorbent body or a portion thereof. The raised barrier may be continuous or discontinuous and may have any suitable thickness and/or height. The raised barrier may be positioned intermediate a topsheet and a backsheet of the absorbent article, may be positioned under the topsheet, or may extend from the topsheet. The raised barrier may function to contain free fluid and other exudates until they can be absorbed by the absorbent body.

In an embodiment, the present disclosure is directed, in part, to an absorbent article comprising a topsheet, a backsheet, and an absorbent body positioned at least partially intermediate the topsheet and the backsheet. The absorbent article comprises a raised barrier that may surround the absorbent body, or a portion thereof, and that defines an internal barrier area in the absorbent article. The raised barrier may extend at least 2 mm and less than 15 mm above a portion of the topsheet positioned within the internal barrier area. The absorbent article comprises a lateral axis, a front waist region on a first side of the lateral axis, a back waist region on a second side of the lateral axis, and a crotch region positioned intermediate the front waist region and the back waist region. The raised barrier extends into the front waist region, the back waist region, and the crotch region. The front waist region has an internal barrier area maximum width measured parallel to the lateral axis and intermediate two most distal, laterally inboard, opposing portions of the raised barrier in the front waist region. The crotch region has an internal barrier area width measured on the lateral axis and intermediate two laterally inboard, opposing portions of the raised barrier in the crotch region. The back waist region has an internal barrier area maximum width measured parallel to the lateral axis and intermediate two most distal, laterally inboard, opposing portions of the raised barrier in the back waist region. The internal barrier area maximum width of the back waist region may be larger than or the same as the internal barrier area width of the crotch region. The internal barrier area maximum width of the back waist region may be larger than, the same, as or smaller than the internal barrier area maximum width of the front waist region.

In an embodiment, the present disclosure is directed, in part, to an absorbent article comprising a topsheet, a backsheet, and an absorbent body positioned at least partially intermediate the topsheet and the backsheet. The absorbent article comprises a raised barrier that may be positioned outboard of the absorbent body and that may at least partially surround the absorbent body. The raised barrier may be positioned intermediate the topsheet and the backsheet. The raised barrier defines an internal barrier area in the absorbent article. A portion of the topsheet positioned over the raised barrier may extend at least 5 mm above a portion of the topsheet positioned within the internal barrier area. The absorbent article comprises a lateral axis, a front waist region on a first side of the lateral axis, a back waist region on a second side of the lateral axis, and a crotch region positioned intermediate the front waist region and the back waist region. The raised barrier extends into the front waist region, the back waist region, and the crotch region. The front waist region has a barrier maximum width measured parallel to the lateral axis and intermediate two most distal, laterally outboard, opposing portions of the raised barrier in the front waist region. The crotch region has a barrier width measured on the lateral axis and intermediate two laterally outboard opposing portions of the raised barrier in the crotch region. The back waist region has a barrier maximum width measured parallel to the lateral axis and intermediate two most distal, laterally outboard, opposing portions of the raised barrier in the back waist region. The barrier maximum width of the back waist region may be larger than or the same as the barrier width of the crotch region. The barrier maximum width of the back waist region may be larger than, smaller than, or the same as the barrier maximum width of the crotch region.

In an embodiment, the present disclosure is directed, in part, to an absorbent article comprising a topsheet, a backsheet, and an absorbent body positioned at least partially intermediate the topsheet and the backsheet. The absorbent article comprises a raised barrier that may be positioned outboard of the absorbent body and that may at least partially surround the absorbent body. The raised barrier may be positioned intermediate the topsheet and the backsheet. The raised barrier defines an internal barrier area in the absorbent article. A portion of the topsheet positioned over the raised barrier may extend at least 2 mm above a portion of the topsheet positioned within the internal barrier area. The portion of the topsheet positioned over the raised barrier may have a different texture, color, or pattern than the remainder of the topsheet. The absorbent article comprises a lateral axis, a longitudinal axis, a front waist region on a first side of the lateral axis, a back waist region on a second side of the lateral axis, and a crotch region positioned intermediate the front waist region and the back waist region. The raised barrier extends into the front waist region, the back waist region, and the crotch region. The front waist region has a first internal barrier area shape, the crotch region has a second internal barrier area shape, and the back waist region has a third internal barrier area shape. The first internal barrier area shape and the third internal barrier area shape may both be different than or the same as the second internal barrier area shape. The raised barrier may be symmetrical or asymmetrical about the lateral axis and/or the longitudinal axis.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIGS. 8-34 are example shapes and configurations of raised barriers and absorbent bodies for use in an absorbent article in accordance with various non-limiting embodiments;

DETAILED DESCRIPTION

Figure 1:
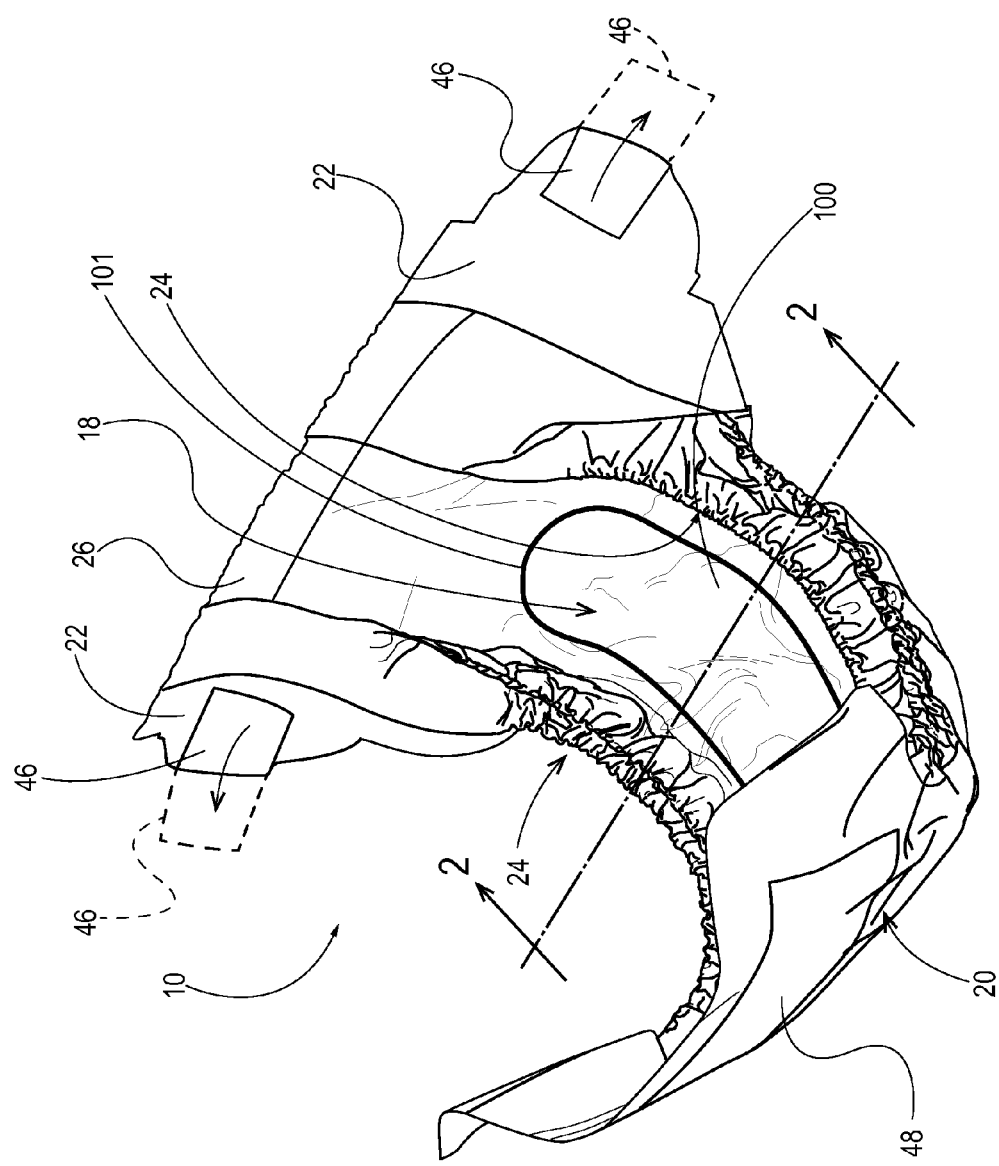
FIG. 1 is a perspective view of an absorbent article in a relaxed condition, wearer-facing surfaces up and having an example raised barrier in accordance with one non-limiting embodiment.

Various non-limiting embodiments of the present disclosure will now be described to provide an overall understanding of the principles of the structure, function, manufacture, and use of the absorbent articles comprising raised barriers disclosed herein. One or more examples of these non-limiting embodiments are illustrated in the accompanying drawings. Those of ordinary skill in the art will understand that the absorbent articles comprising raised barriers described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

"Absorbent article," as used herein, refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments and pads, feminine hygiene pads, and the like.

"Exudates," as used herein, includes, but is not limited to, urine, blood, vaginal discharges, and fecal matter.

"Absorbent body," as used herein, means a structure typically disposed between a topsheet and backsheet of an absorbent article for distributing, absorbing and/or containing exudates received by the absorbent article. The absorbent body comprises an absorbent core and may also comprise additional layers between the topsheet and the backsheet. These additional layers may comprise acquisition layers and other layers of material, for example.

"Absorbent core," as used herein, means a structure typically disposed between a topsheet and backsheet of an absorbent article for absorbing and containing exudates received by the absorbent article. The absorbent core may comprise a cover layer or envelope. The cover layer or envelope may comprise a nonwoven material. In some examples, the absorbent core may comprise an airfelt, a cellulosic material, an absorbent polymer material, and/or a superabsorbent polymer material, for example. The absorbent core may also comprise a thermoplastic adhesive material/composition configured to adhere or immobilize various portions of the absorbent core to one another.

"Absorbent polymer material," and "superabsorbent polymer material," are used herein interchangeably and refer to cross-linked polymeric materials that can absorb at least 5 times their weight of an aqueous 0.9% saline solution as measured using the Centrifuge Retention Capacity test (Edana 441.2-01).

"Airfelt," as used herein, refers to comminuted wood pulp, which is a form of cellulosic fiber.

"Disposable," as used herein, is used in its ordinary sense to mean an article that is disposed or discarded after a limited number of usage events over varying lengths of time, for example, less than about 5 events, less than about 2 events, or, in most instances, after 1 usage event.

"Diaper," as used herein, refers to an absorbent article generally worn by infants and incontinent persons about the lower torso so as to encircle the waist and legs of the wearer and that is specifically adapted to receive and contain urine and fecal matter. The term "diaper" also includes "pants".

"Pant" or "pants" are used interchangeably herein and refer to disposable garments having a waist opening and leg openings designed for infant, child, or adult wearers. A pant may be placed in position on the wearer by inserting the wearer's legs into the leg openings and sliding the pant over the thighs and hips into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants." Suitable pants are disclosed in U.S. Pat. No. 5,246,433, issued to Hasse et al. on Sep. 21, 1993; U.S. Pat. No.

5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al. on Sep. 28, 1999.

"Substantially cellulose free," as used herein, describes an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, and/or absorbency of an absorbent core.

Figure 2:
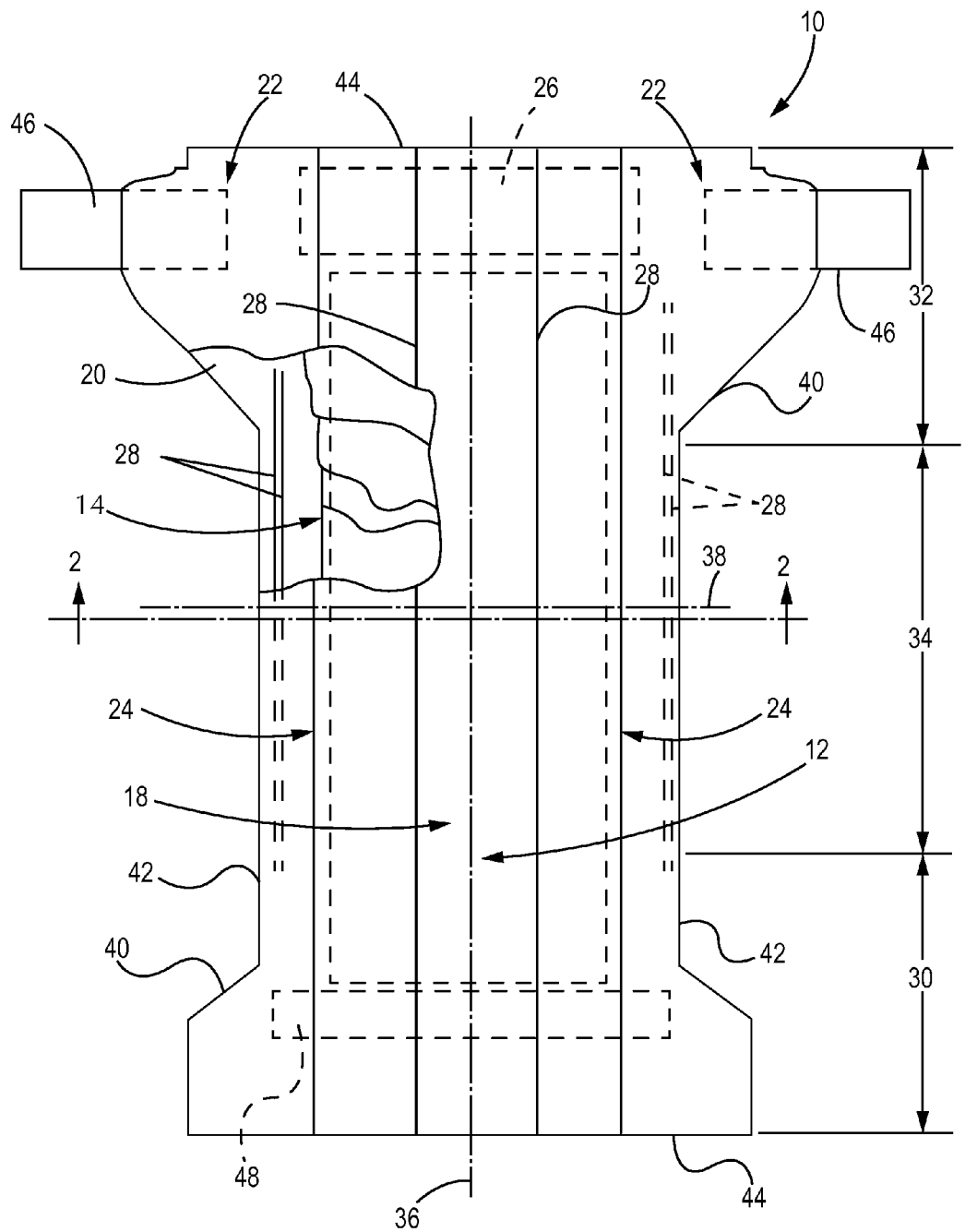
FIG. 2 is a plan view of an absorbent article shown laid out horizontally in a stretched out, flattened state (stretched out against elastic contraction induced by the presence of elastic members), wearer-facing surface oriented toward the viewer without a raised barrier in accordance with one non-limiting embodiment.
Figure 3:
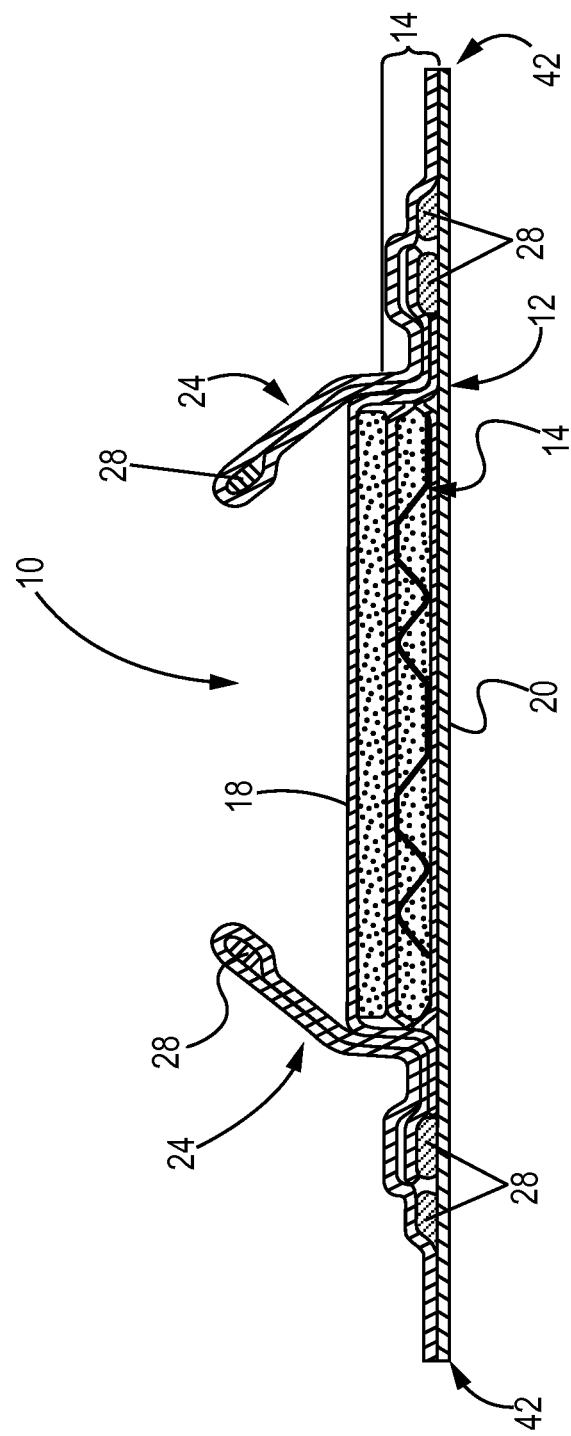
FIG. 3 is an example cross-sectional view of the absorbent article depicted in FIGS. 1 and 2, taken about line 2-2 in those figures, without the raised barrier illustrated, in accordance with one non-limiting embodiment.

FIG. 1 is a perspective view of a diaper 10 in a relaxed, laid-open position as it might appear opened and lying on a horizontal surface. FIG. 2 is a plan view of a diaper 10 shown in a flat-out, uncontracted state (i.e., without elastic induced contraction), shown with portions of the diaper 10 cut away to show underlying structure. The diaper 10 is depicted in FIG. 2 with a longitudinal axis 36 and a lateral axis 38. Portions of the diaper 10 that contact a wearer are shown oriented upwards in FIG. 1, and are shown facing the viewer in FIG. 2. FIG. 3 is a cross-sectional view of the diaper taken at line 2-2 in FIGS. 1 and 2.

The absorbent article, such as diaper 10, may comprise a chassis 12 and absorbent body comprising an absorbent core 14 disposed in the chassis 12. The chassis 12 may comprise the main body of the diaper 10.

The chassis 12 may comprise a topsheet 18, on the wearer-facing surface of the absorbent article, which may be liquid pervious, and a backsheet 20, on the garment-facing surface of the absorbent article, which may be liquid impervious or substantially liquid impervious. The absorbent body comprising the absorbent core 14 may be positioned at least partially intermediate, or fully intermediate, the topsheet 18 and the backsheet 20. The chassis 12 may comprise side panels 22, elasticized leg cuffs 24, and/or an elastic waist feature 26. The chassis 12 may comprise a fastening system, which may comprise at least one fastening member 46 and at least one landing zone 48. The fastening member(s) 46 may be configured to engage the landing zone 48 to attach the absorbent article about a lower torso of a wearer. One or more layers of the topsheet 18 and/or the backsheet 20 may be formed of a nonwoven web or other suitable material.

The elasticized leg cuffs 24 and the elastic waist feature 26 may each typically comprise elastic members 28. One end portion of the diaper 10 may be configured as a front waist region 30 of the diaper 10. An opposite end portion of the diaper 10 may be configured as a back waist region 32 of the diaper 10. An intermediate portion of the diaper 10 may be configured as a crotch region 34, which extends longitudinally intermediate front and back waist regions 30 and 32. Each of the regions 30, 32, and 34 forms ⅓ or 33.33% of the longitudinal length of the diaper 10.

The front and back waist regions 30 and 32 may comprise elastic elements such that they gather about the waist of the wearer to provide improved fit and containment (e.g., elastic waist feature 26). The crotch region 34 is that portion of the diaper 10 which, when the diaper 10 is worn, is generally positioned between the wearer's legs.

The diaper 10 may comprise such other features including front and rear ear panels, waist cap features, elastics, and the like to provide better fit, containment and aesthetic characteristics. Such additional features are described in U.S. Pat. Nos. 3,860,003 and 5,151,092, for example.

In order to apply and keep the diaper 10 in place about a wearer, the second waist region 32 may be attached to the front waist region 30 to form leg openings and an article waist. Here, the fastening members 46 may be engaged with the landing zone 48 to complete the attachment. When fastened, the fastening system carries a tensile load around the article waist.

According to some examples, the diaper 10 may be provided with a re-closable fastening system or may alternatively be provided in the form of a pant. When the absorbent article is a diaper, it may comprise a re-closable fastening system joined to the chassis for securing the diaper to a wearer. When the absorbent article is a pant, the article may comprise at least two side panels joined to the chassis and to each other to form a pant. The fastening system and any component thereof may include any material suitable for such a use, including but not limited to plastics, films, foams, nonwoven, woven, paper, laminates, stretch laminates, activated stretch laminates, fiber reinforced plastics and the like, or combinations thereof. In some examples, the materials making up the fastening system may be flexible. In some examples, the fastening system may comprise cotton or cotton-like materials for additional softness or consumer perception of softness. The flexibility may allow the fastening system to conform to the shape of the body and thus, reduce the likelihood that the fastening system will irritate the wearer's skin.

For unitary absorbent articles, the chassis 12 and the absorbent body comprising the absorbent core 14 may form the main structure of the diaper 10 with other features added to form the composite diaper structure. While the topsheet 18, the backsheet 20, and the absorbent body comprising an absorbent core 14 may be assembled in a variety of well-known configurations, some example diaper configurations are described generally in U.S. Pat. No. 5,554,145, entitled "Absorbent Article With Multiple Zone Structural Elastic-Like Film Web Extensible Waist Feature," issued to Roe et al. on Sep. 10, 1996; U.S. Pat. No. 5,569,234, entitled "Disposable Pull-On Pant," issued to Buell et al. on Oct. 29, 1996; and U.S. Pat. No. 6,004,306, entitled "Absorbent Article With Multi-Directional Extensible Side Panels," issued to Robles et al. on Dec. 21, 1999.

The topsheet 18 may be fully or partially elasticized and/or may be foreshortened to create a void space between the topsheet 18 and the absorbent body comprising the absorbent core 14. Example structures including elasticized or foreshortened topsheets are described in more detail in U.S. Pat. No. 5,037,416, entitled "Disposable Absorbent Article Having Elastically Extensible Topsheet," issued to Allen et al. on Aug. 6, 1991; and U.S. Pat. No. 5,269,775, entitled "Trisection Topsheets for Disposable Absorbent Articles and Disposable Absorbent Articles Having Such Trisection Topsheets," issued to Freeland et al. on Dec. 14, 1993.

The backsheet 20 may be joined with the topsheet 18 or to at least a portion of the topsheet 18. The backsheet 20 may serve to prevent, or at least inhibit, the exudates absorbed by the absorbent body comprising the absorbent core 14 and contained within the diaper 10 from soiling other external articles that may contact the diaper 10, such as bed sheets and clothing. The backsheet 20 may be substantially impervious to liquids (e.g., urine and runny fecal matter) and may be formed of a laminate of a nonwoven and a thin polymeric film such as a thermoplastic film having a thickness of about 0.012 mm (0.5 mil) to about 0.051 mm (2.0 mils), for example. The nonwoven may be a nonwoven web as described herein. Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing, or at least inhibiting, liquid exudates from passing through the backsheet 20. Example breathable materials may include materials such as woven webs, nonwoven webs, composite materials such as film-coated nonwoven webs, and microporous films such as manufactured by Mitsui Toatsu Co., of Japan under the designation ESPOIR and by EXXON Chemical Co., of Bay City, Tex., under the designation EXXAIRE. Suitable breathable composite materials comprising polymer blends are available from Clopay Corporation, Cincinnati, Ohio under the name HYTREL blend P1 8-3097. Other examples of such breathable composite materials are described in greater detail in PCT Application No. WO 95/16746, published on Jun. 22, 1995 in the name of E.I. DuPont. Other breathable backsheets including nonwoven webs and apertured formed films are described in U.S. Pat. No. 5,571,096, issued to Dobrin et al. on Nov. 5, 1996. Other suitable backsheets are described in U.S. Patent Publication No. 2008/0125739 to Lodge et al.

Suitable nonwoven web materials useful in various components of the absorbent articles include, but are not limited to, spunbond, meltblown, spunmelt, solvent-spun, electro-spun, carded, film fibrillated, melt-film fibrillated, air-laid, dry-laid, wet-laid staple fibers, and other nonwoven web materials formed in part or in whole of polymer fibers, as known in the art. A suitable nonwoven web material may also be an SMS material, comprising a spunbonded, a melt-blown and a further spunbonded stratum or layer or any other combination of spunbonded and melt-blown layers, such as a SMMS or SSMMS etc. Examples include one or more layers of fibers with diameters below 1 micron (nanofibers and nanofiber layers); examples of these rise in combinations of SMS, SMNS, SSMNS or SMNMS nonwoven webs (where "N" designates a nanofiber layer). In some examples, permanently hydrophilic nonwovens, and in particular, nonwovens with durably hydrophilic coatings may be desirable. Typically, the suitable nonwoven may be air permeable. The suitable nonwoven may be water or liquid permeable or may be water impermeable by reason of fiber size, density, and hydrophobicity of the fibers. Water or liquid permeability of the nonwovens may be enhanced by treatments to render the fibers hydrophilic.

The nonwoven webs may be formed predominately of polymeric fibers. In some examples, suitable nonwoven fiber materials may include, but are not limited to, polymeric materials, such as polyolefins, polyesters, polyamide, or specifically polypropylene (PP), polyethylene (PE), polylactic acid (PLA), polyethylene terephthalate (PET), and/or blends thereof. Nonwoven fibers may be formed of, or may include as additives or modifiers, components such as aliphatic polyesters, thermoplastic polysaccharides, or other biopolymers (bio-based or renewable polymers).

The individual fibers may be monocomponent or multicomponent fibers. The multicomponent fibers may be bicomponent, such as in a core-and-sheath or side-by-side arrangement. Often, the individual components comprise aliphatic polyolefins such as polypropylene or polyethylene, or their copolymers, aliphatic polyesters, thermoplastic polysaccharides or other biopolymers.

Further useful nonwovens, fiber compositions, formations of fibers and nonwovens and related methods are described in U.S. Pat. No. 6,645,569 to Cramer et al., U.S. Pat. No. 6,863,933 to Cramer et al., U.S. Pat. No. 7,112,621 to Rohrbaugh et al.; U.S. patent application Ser. Nos. 10/338, 603 and 10/338,610 by Cramer et al.; Ser. No. 13/005,237 by Lu et al.; and Ser. No. 13/428,404 by Xu et al.

In order to enhance softness perceptions of the absorbent article, nonwovens forming the backsheet may be hydroenhanced or hydroengorged. Hydroenhanced/hydroengorged nonwovens are described in U.S. Pat. Nos. 6,632,385 and 6,803,103, and U.S. Pat. App. Pub. No. 2006/0057921.

A nonwoven may also be treated by a "selfing" mechanism. By "selfing" nonwovens, high densities of loops (>150 in 2) may be formed which protrude from the surface of the nonwoven substrate. Since these loops act as small flexible brushes, they create an additional layer of springy loft, which may enhance softness. Nonwovens treated by a selfing mechanism are described in U.S. Pat. App. Pub. No. US 2004/0131820.

Any of the nonwoven types described herein may be used for the topsheet, backsheet, outer layer, barrier cuff, loops component in a hook-and-loop fastening system of an absorbent article, or any other portion of a manufactured article such as cleansing wipes and other personal hygiene products, dusters and dusting cloths, household cleaning cloths and wipes, laundry bags, dryer bags and sheets comprising a layer formed of nonwoven web.

In an embodiment, an absorbent article includes an absorbent body comprising an absorbent core 14 that is substantially cellulose free, as described in U.S. Pat. No. 7,750,203; U.S. Pat. No. 7,744,576, and U.S. Patent Publication No. 2008/0312617A1. Absorbent cores 14 comprising airfelt or other materials are also within the scope of the present disclosure. Further, any cores known to those of skill in the art may be provided in the absorbent articles of the present disclosure.

Figure 4:
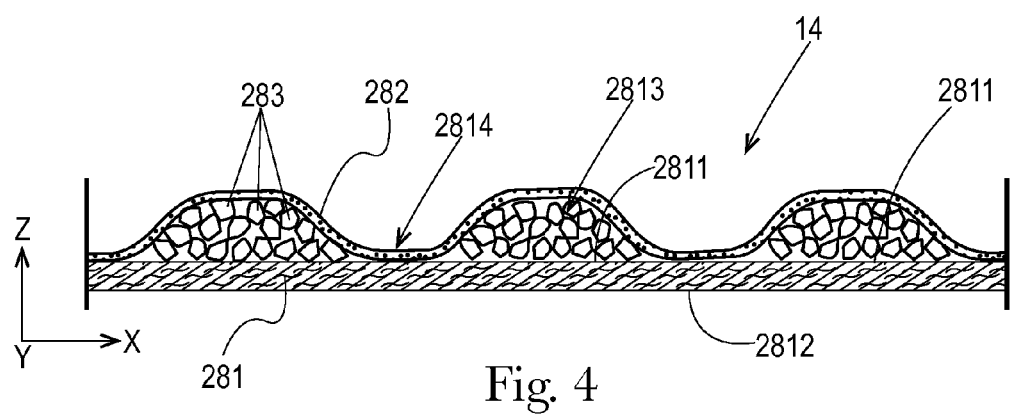
FIG. 4 is a schematic cross-sectional view of an example of an absorbent core in accordance with one non-limiting embodiment.
Figure 5:
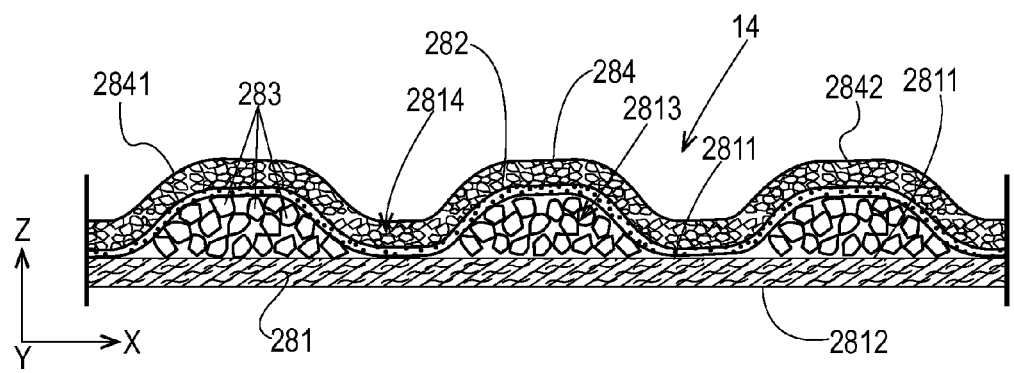
FIG. 5 is a schematic cross-sectional view of another example of an absorbent core in accordance with one non-limiting embodiment.
Figure 6:
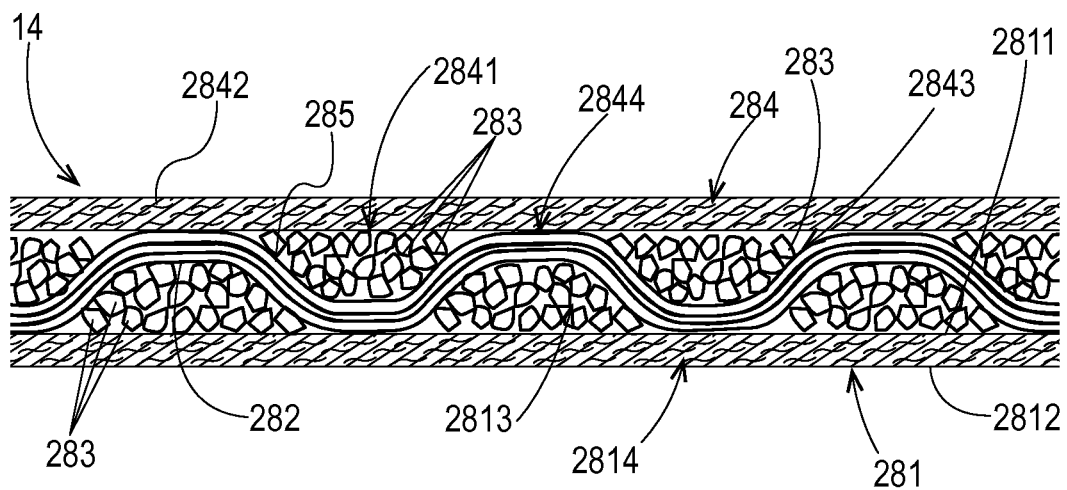
FIG. 6 is a schematic cross-sectional view of another example of an absorbent core in accordance with one non-limiting embodiment.

Cross-sectional views of examples of suitable absorbent cores are schematically represented in FIGS. 4-6. In an embodiment, an absorbent core 14 comprises first and second layers of material 281, 282 and an absorbent material 283 disposed between the first and second layers of material 281, 282. In an embodiment the first and second layers of material can be a fibrous material chosen from at least one of a nonwoven fibrous web, a woven fibrous web and a layer of thermoplastic adhesive material. Although the first and second layers of material 281, 282 may be made of a same material, in an embodiment, the first layer of material 281 is a nonwoven fibrous web and the second layer of material 282 is a layer of thermoplastic adhesive material. A nonwoven fibrous web 281 can include synthetic fibers, such as mono-constituent fibers of PE, PET and PP, multi-constituent fibers such as side by side, core/sheath or island in the sea type fibers. Such synthetic fibers may be formed via a spunbonding process or a meltblowing process. The nonwoven fibrous web 281 may include a single layer of fibers but it may also be advantageous to provide the nonwoven web with multiple layers of fibers such as multiple layers of spunbond fibers, multiple layers of meltblown fibers or combinations of individual layer(s) of spunbond and meltblown fibers. In an embodiment, the nonwoven fibrous web 281 may be treated with an agent (such as a surfactant) to increase the surface energy of the fibers of the web. Such an agent renders the nonwoven web more permeable to liquids such as urine. In another embodiment, the nonwoven web can be treated with an agent (such as a silicone) that lowers the surface energy of the fibers of the nonwoven web. Such an agent renders the nonwoven web less permeable to liquids such as urine.

The first layer of material 281 comprises a first surface 2811 and a second surface 2812 and at least regions 2813 of the first surface are in direct facial relationship with a significant amount of absorbent material 283. In an embodiment an absorbent material is deposited on the first surface 2811 in a pattern to form regions 2813 on the first layer 281, which are in direct facial relationship with a significant amount of absorbent polymer material 283 and regions 2814 on the first web that are in facial relationship with only an insignificant amount of absorbent material. By "direct facial relationship with a significant amount of absorbent material" it is meant that some absorbent material is deposited on top of the regions 2813 at a basis weight of at least 100 g/m$^2$, at least 250 g/m$^2$, or even at least 500 g/m$^2$. The pattern may include regions that all have the same shape and dimensions (i.e., projected surface area and/or height). In the alternative, the pattern may include regions that have different shape or dimensions to form a gradient of regions.

In an embodiment, the second layer 282 may be a layer of a thermoplastic adhesive material. "Thermoplastic adhesive material" as used herein is understood to mean a polymer composition from which fibers are formed and applied to the absorbent material with the intent to immobilize the absorbent material in both the dry and wet state. Non-limiting examples of thermoplastic adhesive material may comprise a single thermoplastic polymer or a blend of thermoplastic polymers. The thermoplastic adhesive material may also be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $-6°$ C.$>$Tg$<16°$ C. In certain embodiments, typical concentrations of the polymer in a hot melt are in the range of about 20% to about 40% by weight. Example polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are polymers prepared using single-site or metallocene catalysts. In example embodiments, the tackifying resin has typically a Mw below 5,000 and a Tg usually above room temperature, typical concentrations of the resin in a hot melt are in the range of about 30 to about 60% by weight, and the plasticizer has a low Mw of typically less than 1,000 and a Tg below room temperature, with a typical concentration of about 0% to about 15%.

The thermoplastic adhesive material 282 can be disposed substantially uniformly within the absorbent material 283. In the alternative, the thermoplastic adhesive material 282 can be provided as a fibrous layer disposed on top of the absorbent material 283 and the regions 2814 of the first surface 2811 that are in facial relationship with only an insignificant amount of absorbent material. In an embodiment, a thermoplastic adhesive material is applied at an amount of between 1 and 20 g/m$^2$, between 1 and 15 g/m$^2$, or even between 2 and 8 g/m$^2$. The discontinuous deposition of absorbent material on the first layer 281 imparts an essentially three-dimensional structure to the fibrous layer of thermoplastic material 282. In other words, the layer of thermoplastic adhesive material follows the topography resulting from the absorbent material 283 deposited on the first nonwoven fibrous web 281 and the regions 2814 that only include insignificant amounts of absorbent material. Without intending to be bound by any theory, it is believed that the thermoplastic adhesive materials disclosed herein enhance immobilization of the absorbent material in a dry and wet state.

In an embodiment, the absorbent core 14 may comprise a second layer of a nonwoven fibrous material 284. This second layer may be provided of the same material as the nonwoven fibrous layer 281, or in the alternative may be provided from a different material. It may be advantageous for the first and second nonwoven fibrous layers 281, 284 to be different in order to provide these layers with different functionalities.

The regions 2813 may have any suitable shape in the x-y dimension of the absorbent core. In an embodiment, the regions 2813 form a pattern of disc that are spread on the first surface of the first web 281. In an embodiment, the regions 2813 form a pattern of longitudinal "strips" that extend continuously along the longitudinal axis of the absorbent core (i.e. along the y dimension). In an alternative embodiment, these strips may be are arranged to form an angle of at between 10 and 90 degrees, between 20 and 80 degrees, between 30 and 60 degrees, or even 45 degrees relative to the longitudinal axis of the absorbent article, specifically reciting all 1 degree increments within the specified ranges and all ranged created therein or thereby.

In an embodiment, the second nonwoven layer 284 has a first surface 2841 and a second surface 2842 and an absorbent material 283 applied to its first surface 2841 in order to form a pattern of regions 2843 that are in direct facial relationship with a significant amount of absorbent material 283 and regions 2844 on the first surface 2841 that are in facial relationship with only an insignificant amount of absorbent material as previously discussed. In an embodiment, a thermoplastic adhesive material 285 may further be applied on top of the second nonwoven layer 284 as previously discussed in the context of the first web/absorbent material/thermoplastic adhesive material composite. The second nonwoven layer 284 may then be applied on top of the first nonwoven layer 281. In an embodiment, the pattern of absorbent material present on the second nonwoven layer 284 may be the same as the pattern of absorbent material present on the first nonwoven layer 281. In another embodiment, the patterns of absorbent material that are present on the first and second nonwoven layers are different in terms of at least one of the shape of the regions, the projected surface areas of the regions, the amount of absorbent material present on the regions, and the type of absorbent material present on the regions.

The absorbent core 14 may also comprise an auxiliary adhesive which is not illustrated in the figures. The auxiliary adhesive may be deposited on at least one of or even both the first and second nonwoven layers 281, 284 before application of the absorbent material 283 in order to enhance adhesion of the absorbent material as well as adhesion of the thermoplastic adhesive material 282, 285 to the respective nonwoven layers 281, 284. The auxiliary adhesive may also aid in immobilizing the absorbent material and may comprise the same thermoplastic adhesive material as described hereinabove or may also comprise other adhesives including but not limited to sprayable hot melt adhesives, such as H.B.

Fuller Co. (St. Paul, Minn.) Product No. HL-1620-B. The auxiliary adhesive may be applied to the nonwoven layers 281, 284 by any suitable means, but according to certain embodiments, may be applied in about 0.5 to about 1 mm wide slots spaced about 0.5 to about 2 mm apart. Non-limiting examples of suitable absorbent material 283 include absorbent polymer material such as cross linked polymeric materials that can absorb at least 5 times their weight of an aqueous 0.9% saline solution as measured using the Centrifuge Retention Capacity test (Edana 441.2-01). In an embodiment, the absorbent material 283 is absorbent polymer material which is in particulate form so as to be flowable in the dry state.

Figure 7:
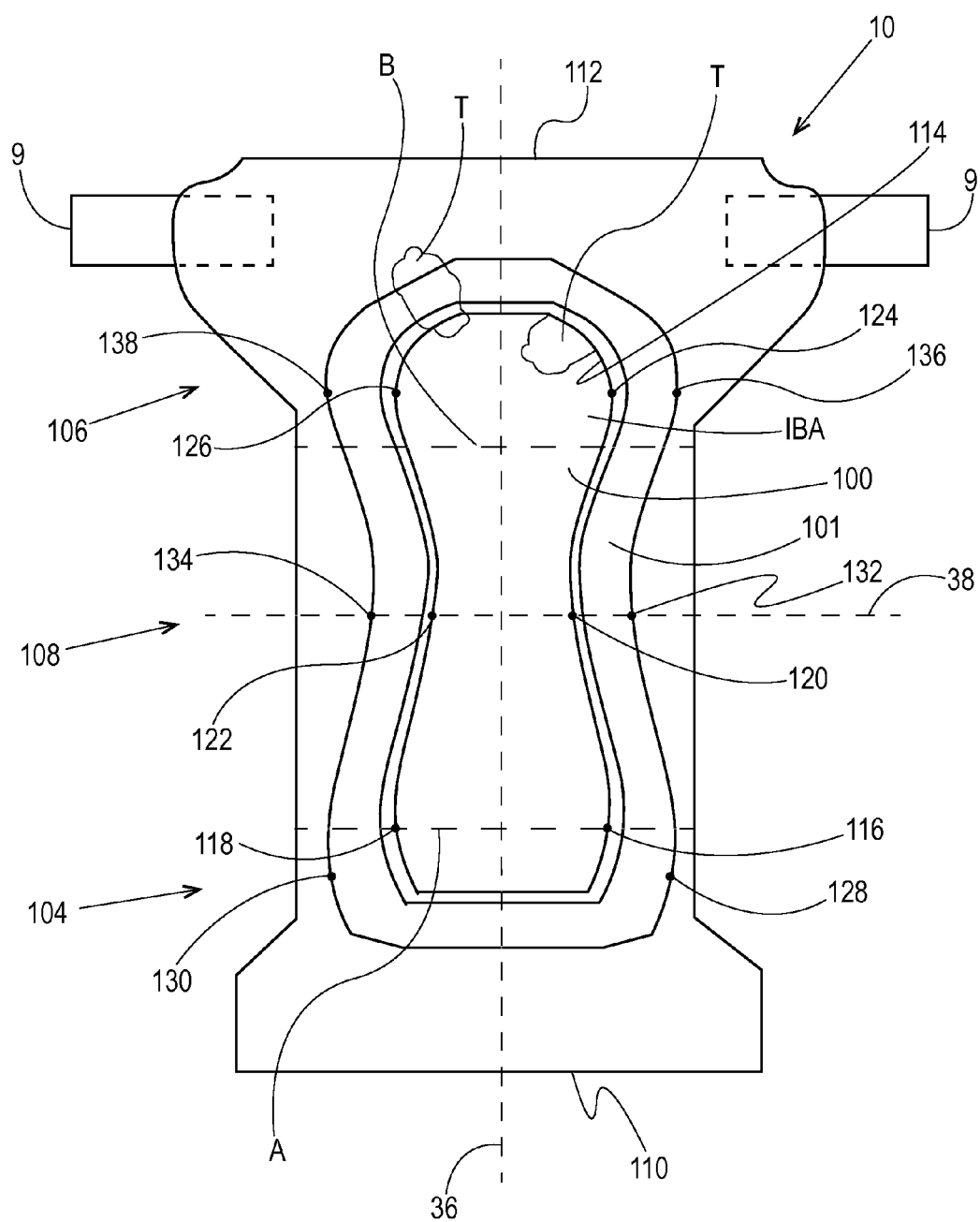
FIG. 7 is a plan view of an example absorbent article shown laid out horizontally in a stretched out, flattened state (stretched out against elastic contraction induced by the presence of elastic members), wearer-facing surface oriented toward the viewer and having a raised barrier in accordance with one non-limiting embodiment.

In an embodiment, referring to FIG. 7, the present disclosure is directed to absorbent articles, such as a diaper 10, comprising an absorbent body 100 and one or more raised barriers 101 extending from a wearer-facing surface of the absorbent body (as shown in FIG. 7). If more than one raised barrier is provided, there may be an outer raised barrier and an inner raised barrier. In one instance, the outer and/or inner raised barrier may be discontinuous in portions of its perimeter. FIG. 7 shows the raised barrier 101 and the absorbent body 100 on a diaper 10 having fastening components 9. The fastening components 9 are configured to attach a back waist region 106 of the diaper 10 to a front waist region 104 of the diaper 10 to form two leg openings and a waist opening. The fastening components 9 may be configured to attach to a landing zone on the front waist region 104, much like or the same as the landing zone 48 of FIG. 1. Pants, sanitary napkins, and other absorbent articles are also contemplated within the scope of the present disclosure, although the diaper 10 is illustrated as an example embodiment. The raised barrier 101 may surround, surround a portion of, or partially surround the absorbent body 100. The raised barrier 101 may be positioned outboard of the absorbent body 100. In other embodiments, the raised barrier 100 may be positioned on or overlay a portion of the absorbent body 100 and surround a central portion of the absorbent body 100. In an embodiment, the raised barrier 101 may fully surround a perimeter of the absorbent body 100 or fully surround a portion of the perimeter of the absorbent body 100. The raised barrier 101 may still be considered to surround the absorbent body 100 even if the raised barrier 101 is on a different layer of the diaper 10 with the absorbent body 100 positioned inboard thereof.

The raised barrier of the present disclosure may be useful in reducing exudate leakage from the absorbent article as it provides the absorbent article with the ability to contain excreted exudates until they can be absorbed by the absorbent body. For example, during a urine gush from a wearer, the absorbent body may not be able to absorb all of the urine at once. To prevent, or at least inhibit, the urine leaking from the absorbent article, the raised barrier can contain the urine over the absorbent body 100 until the absorbent body can absorb it. The same scenario applies to viscous fecal matter, blood, or other bodily fluids.

The raised barrier 101 may be formed with at least a portion of the absorbent body 100 or may be a separate structure from the absorbent body 100. In an embodiment, the raised barrier 101 may be formed of at least some of the same materials as the absorbent body 100 (e.g., acquisition layer, absorbent core) such that the raised barrier 101 may absorb at least some exudates discharged from a wearer of the absorbent article 10. In other embodiments, the raised barrier 101 may be configured to be impermeable, or substantially impermeable to exudates.

The raised barriers of the present disclosure may be made of any suitable materials, such as plastics, foams, nonwovens, and/or cellulosic materials, for example. In an embodiment, at least a portion of, or all of, the raised barrier may comprise a compressible, resilient material, such as a foam, a laminated nonwoven, a high loft structure, an elastomer, a cellulose material, an absorbent material, a treated fiber material, a fluid distribution material, and combinations thereof. The raised barrier may be covered by, or surrounded by, a web, such as a nonwoven web, for example. The raised barrier may have a different pore size, density, and/or surface energy as compared to surrounding materials of the diaper 10 or the absorbent body 100.

The raised barrier 101 may be positioned intermediate the topsheet 18 and the backsheet 20, may be positioned under a portion of the topsheet 18, or may be positioned on a wearer-facing surface of the topsheet 18. In any event, the raised barrier 101 may extend outwardly from a plane of the wearer-facing surface of the topsheet 18. Stated another way, the raised barrier 101 may extend toward the wearer more than a portion of the topsheet 18 covering a central portion of the absorbent body 100. In the event that the raised barrier 101 is positioned on a wearer-facing surface of the topsheet 18, it may be attached to the topsheet 18, adhesively attached to the topsheet 18, bonded to the topsheet 18, melted to the topsheet 18, or otherwise engaged with the topsheet 18 using any suitable techniques known to those of skill in the art. Even if the raised barrier 101 is not positioned under the topsheet 18, it still may be covered by a soft material or web, such a nonwoven, so as to not irritate a wearer's skin. In such an embodiment, the soft material or web may be attached to, bonded to, melted to, or otherwise engaged with the topsheet 18 to form a pocket extending from the topsheet 18 toward the wearer. The pocket may hold the raised barrier 101 to, or proximate to, a wearer-facing surface of the topsheet 18 without the raised barrier 101 being physically attached to the topsheet 18. Stated another way, the raised barrier may merely rest on the topsheet 18 within the pocket, but not actually be itself attached to the topsheet 18.

Referring again to FIG. 7, the diaper 10 comprises a front waist region 104, a back waist region 106, and a crotch region 108 positioned longitudinally intermediate the front waist region 104 and the back waist region 106. The various regions are indicated by dashed lines in FIG. 7. FIG. 7 is not to scale. The front waist region 104, the back waist region 106, and the crotch region 108 each form ⅓ or 33.33% of the overall longitudinal length of the absorbent article 10 measured from the front waist end edge 110 to the back waist end edge 112. This measuring system for the various regions applies to all the embodiments herein. To measure the overall longitudinal length of the absorbent article 10, a person would position the absorbent article 10 on a flat surface in a flat, laid out position (no elastic contraction), and measure the distance, using a measuring tape, from the front waist end edge 110 to the back waist end edge 112 along the longitudinal axis 36. That distance divided by 3 is the longitudinal length of each region 104, 106, and 108.

The diaper 10 has a lateral axis 38 extending through its longitudinal midpoint and a longitudinal axis 36 extending through its lateral midpoint. The front waist region 104 is positioned on a first side of the lateral axis 38. The back waist region 106 is positioned on a second side of the lateral axis 38 and the crotch region 108 is positioned intermediate the front waist region 104 and the back waist region 106. The lateral axis 38 crosses the midpoint of the longitudinal axis 36 and the longitudinal axis 36 crosses the midpoint of the lateral axis 38. The lateral axis 38 extends in a direction perpendicular to the longitudinal axis 36.

The raised barrier 101 forms or defines an internal barrier area in the diaper 10. The internal barrier area is indicated in FIG. 7 as IBA. The internal barrier area is the portion of the diaper 10 over the absorbent body 100 that is inboard of the internal perimeter 114 of the raised barrier 101. The internal barrier area may extend at least in part into the front waist region 104, the crotch region 108, and the back waist region 106 or one or more of these regions. In an embodiment, the absorbent body 100 may be positioned completely within the internal perimeter 114. In other embodiments, the absorbent body 100 may extend under at least a portion of the raised barrier 101 and extend inboard of the internal perimeter 114. In FIG. 7, the absorbent body 100 may be covered by one or more topsheets "T" and the raised barrier 101 may or may not be covered by the one or more topsheets T. Only portions of the topsheet T are illustrated in FIG. 7, although it is to be understood that the topsheet T may span the entire wearer-facing surface of the diaper 10 or may span less than the entire wearer-facing surface of the diaper 10.

The dashed lines in FIG. 7 (not including the lateral axis 36 and the longitudinal axis 38) demarcate the front 104, back 106, and crotch regions 108 of the diaper 10. To take particular measurements on the diaper 10, as discussed below, it may be useful to draw these lines on an absorbent article to be tested. First, the absorbent article should be attached to a flat surface in a flat, laid out state, wearer-facing surface oriented toward the tester and away from the flat surface. Next, using a measuring tape, measure the longitudinal length of the diaper 10 from the front waist end edge 110 to the back waist end edge 112 along the longitudinal axis 36 and divide the result by 3. This is the longitudinal length of each region or L. Next, measure from the front waist end edge 110 longitudinally inward on the longitudinal axis 36 until L is reached and place a dot on the diaper 10 at the point L is reached. Draw a line (A) intersecting the dot and parallel to the lateral axis 38. Line A separates the front waist region 104 from the crotch region 108. From line A, measure along the longitudinal axis 36 the distance L again and place a dot on the diaper 10 at the point L is reached. Draw a line (B) intersecting the dot and parallel to the lateral axis 38. Line B separates the crotch region 108 from the back waist region 106. The diaper 10 is now divided into three equal, or substantially equal, longitudinally extending sections defining the front, back, and crotch regions 104, 106, and 108.

The front waist region 104 has an internal barrier area maximum width (i.e., lateral width) measured parallel to the lateral axis 38 and intermediate two laterally inboard, most distal opposing portions of the raised barrier 101. The two laterally inboard, most distal, opposing portions are indicated as 116 and 118 in FIG. 7 as an example. Although, these two portions are on line A, they could also be at other places in the front waist region 104 in other embodiments depending on the shape of the internal barrier area within the front waist region 104. To determine where the internal barrier maximum width is in the front waist region 104, use the measuring tape and position it parallel to the lateral axis 38. Find the laterally widest portion of the internal barrier area in the front waist region 104 and record a width to the closest +/−1.0 mm. This number is the internal barrier area maximum width in the front waist region 104.

The crotch region 108 has an internal barrier area width (not necessarily the maximum lateral width) measured on and parallel to the lateral axis 38 and intermediate two laterally inboard, opposing portions of the raised barrier 101. The two laterally inboard, opposing portions are indicated as 120 and 122 in FIG. 7 as an example. Using the measuring tape, measure the distance between portions 120 and 122 and record a width to the closest +/−1.0 mm. This number is the internal barrier area width in the crotch region 108 along the lateral axis 38.

The back waist region 106 has an internal barrier area maximum width (i.e., lateral width) measured parallel to the lateral axis 38 and intermediate two laterally inboard, opposing portions of the raised barrier 101. The two laterally inboard, most distal, opposing portions are indicated as 124 and 126 in FIG. 7 as an example. The two laterally inboard, most distal, opposing portions 124 and 126 may be at other locations in other embodiments depending on the shape of internal barrier area in the back waist region 106. To determine where the internal barrier maximum width is in the back waist region 106, use the measuring tape and position it parallel to the lateral axis 38. Find the laterally widest portion of the internal barrier area in the back waist region 106 and record a width to the closest +/1.0 mm. This number is the internal barrier area maximum width in the back waist region 104.

In various embodiments, the internal barrier area maximum width of the back waist region 106 may be larger than the internal barrier area width of the crotch region 108 and may be larger than the internal barrier area maximum width of the front waist region 104. In other embodiments, the internal barrier area maximum width of the back waist region 106 may be the same as the internal barrier area maximum width of the front waist region 104 and/or may be the same as the internal barrier width of the crotch region 108. In still other embodiments, the internal barrier area maximum width of the front waist region 104 may be larger than the internal barrier area maximum width of the back waist region 106 and/or may be larger than the internal barrier area width of the crotch region 108.

In an embodiment, the ratio of the internal barrier area maximum width of the back waist region 106 to the internal barrier area width of the crotch region 108 may be about 4 to about 0.5, about 3 to about 0.8, about 2.5 to about 1, about 2.4 to about 1.1, about 2.1 to 1, about 2 to about 1, about 1.5 to about 1, about 1 to 1, about 0.5 to about 4, about 3 to about 0.8, about 1 to about 2.5, about 1.1 to about 2.4, about 1 to about 2, or about 1 to about 1.5, specifically reciting all 0.1 increments within the above specified ranges and any ranges formed therein or thereby. In some embodiments, the ratio of the internal barrier area maximum width of the back waist region 106 to the internal barrier area maximum width of the front waist region 104 may be about 3 to about 0.5, about 2 to about 1, about 1.5 to about 1, about 1.3 to about 1, about 1.1 to 1, about 1 to about 1, about 0.5 to about 3, about 1 to about 2, about 1 to about 1.5, about 1 to about 1.3, or about 1 to about 1.1, specifically reciting all 0.1 increments within the above-specified ranges and any ranges formed therein or thereby. In an embodiment, the ratio of the internal barrier area maximum width of the front waist region 104 to the internal barrier area width of the crotch region 108 may be about 4 to about 0.5, about 3 to about 0.8, about 2.5 to about 1, about 2.4 to about 1.1, about 2.1 to about 1, about 2 to about 1, about 1.5 to about 1, about 1 to 1, about 0.5 to about 4, about 3 to about 0.8, about 1 to about 2.5, about 1.1 to about 2.4, about 1 to about 2, or about 1 to about 1.5, specifically reciting all 0.1 increments within the above specified ranges and any ranges formed therein or thereby.

The front waist region 104 has a barrier maximum width (i.e., lateral width) measured parallel to the lateral axis 38 and intermediate two most distal, laterally outboard, opposing portions of the raised barrier 101. The two laterally outboard, most distal, opposing portions are indicated as 128 and 130 in FIG. 7 as an example. These two portions 128 and 130 could be located at other places in the front waist region 104 in other embodiments depending on the shape and thickness of the raised barrier 101 in the front waist region 104. To determine where the barrier maximum width is in the front waist region 104, use the measuring tape and position it parallel to the lateral axis 38. Find the laterally widest portion of the raised barrier 101 in the front waist region 104 and record a width to the closest +/1.0 mm. This number is the barrier maximum width in the front waist region 104.

The crotch region 108 has an barrier width (not necessarily the maximum lateral width) measured on and parallel to the lateral axis 38 and intermediate two laterally outboard, opposing portions of the raised barrier 101. The two laterally outboard, opposing portions are indicated as 132 and 134 in FIG. 7 as an example. Using the measuring tape, measure the distance between portions 132 and 134 and record a width to the closest +/−1.0 mm. This number is the barrier width in the crotch region 108 along the lateral axis 38.

The back waist region 106 has a barrier maximum width (i.e., lateral width) measured parallel to the lateral axis 38 and intermediate two most distal, laterally outboard, opposing portions of the raised barrier 101. The two laterally outboard, most distal, opposing portions are indicated as 136 and 138 in FIG. 7 as an example. These two portions 136 and 138 could be located at other places in the back waist region 106 in other embodiments depending on the shape and thickness of the raised barrier 101 in the back waist region 104. To determine where the barrier maximum width is in the back waist region 106, use the measuring tape and position it parallel to the lateral axis 38. Find the laterally widest portion of the raised barrier 101 in the back waist region 106 and record a width to the closest +/1.0 mm. This number is the barrier maximum width in the back waist region 106.

In various embodiments, the barrier maximum width of the back waist region 106 may be larger than the barrier width of the crotch region 108 and may be larger than the barrier maximum width of the front waist region 104. In other embodiments, the barrier maximum width of the back waist region 106 may be the same as the barrier maximum width of the front waist region 104 and/or may be the same as the barrier width of the crotch region 108. In still other embodiments, the barrier maximum width of the front waist region 104 may be larger than the barrier maximum width of the back waist region 106 and/or may be larger than the barrier area of the crotch region 108.

In an embodiment, the ratio of the barrier maximum width of the back waist region 106 to the barrier width of the crotch region 108 may be about 4 to about 0.5, about 3 to about 0.8, about 2.5 to about 1, about 2.4 to about 1.1, about 2.1 to about 1, about 2 to about 1, about 1.5 to about 1, about 1 to about 1, about 0.5 to about 4, about 3 to about 0.8, about 1 to about 2.5, about 1.1 to about 2.4, about 1 to about 2, or about 1 to about 1.5, specifically reciting all 0.1 increments within the above specified ranges and any ranges formed therein or thereby. In some embodiments, the ratio of the barrier maximum width of the back waist region 106 to the barrier maximum width of the front waist region 104 may be about 3 to about 0.5, about 2 to about 1, about 1.5 to about 1, about 1.3 to about 1, about 1.1 to about 1, about 1 to about 1, about 0.5 to about 3, about 1 to about 2, about 1 to about 1.5, about 1 to about 1.3, or about 1 to about 1.1, specifically reciting all 0.1 increments within the above specified ranges and any ranges formed therein or thereby. In an embodiment, the ratio of the barrier maximum width of the front waist region 104 to the barrier width of the crotch region 108 may be about 4 to about 0.5, about 3 to about 0.8, about 2.5 to about 1, about 2.4 to about 1.1, about 2.1 to about 1, about 2 to about 1, about 1.5 to about 1, about 1 to about 1, about 0.5 to about 4, about 3 to about 0.8, about 1 to about 2.5, about 1.1 to about 2.4, about 1 to about 2, or about 1 to about 1.5, specifically reciting all 0.1 increments within the above specified ranges and any ranges formed therein or thereby.

In an embodiment, the raised barrier 101 may have a thickness (i.e., outboard portion of raised barrier 101 to inboard portion of the raised barrier 101) in the range of about 1 mm to about 70 mm, about 2 mm to about 50 mm, about 2 mm to about 40 mm, about 10 mm, about 15 mm, about 20 mm, or about 25 mm, specifically reciting all 0.1 mm increments within the above-specified ranges and any ranges formed therein or thereby. The thickness of the raised barrier 101 may be constant, substantially constant, or may vary. As an example, the thickness of the raised barrier 101 in the front waist region 104 may be less than the thickness of the raised barrier 101 in the crotch region 108 and/or the back waist region 106. The thicknesses may vary based on which type of exudates (e.g., urine, fecal matter) portions of the raised barriers are designed to contain.

Figure 8:
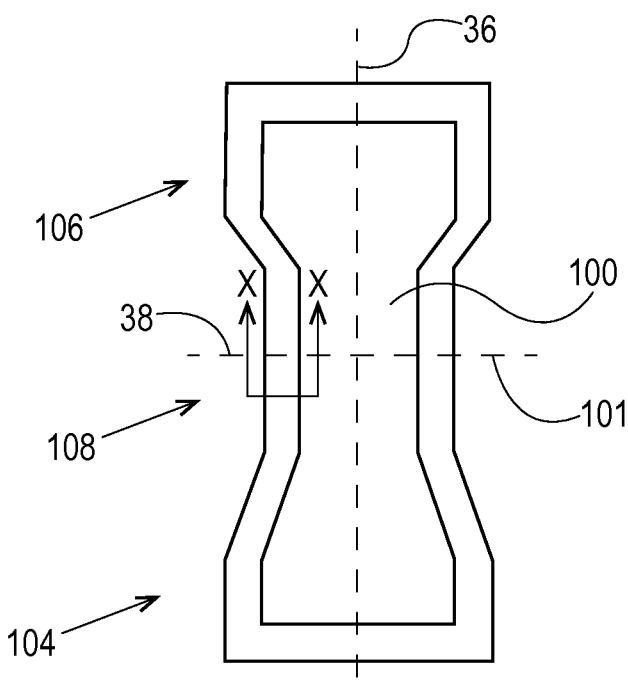
Figure 9:
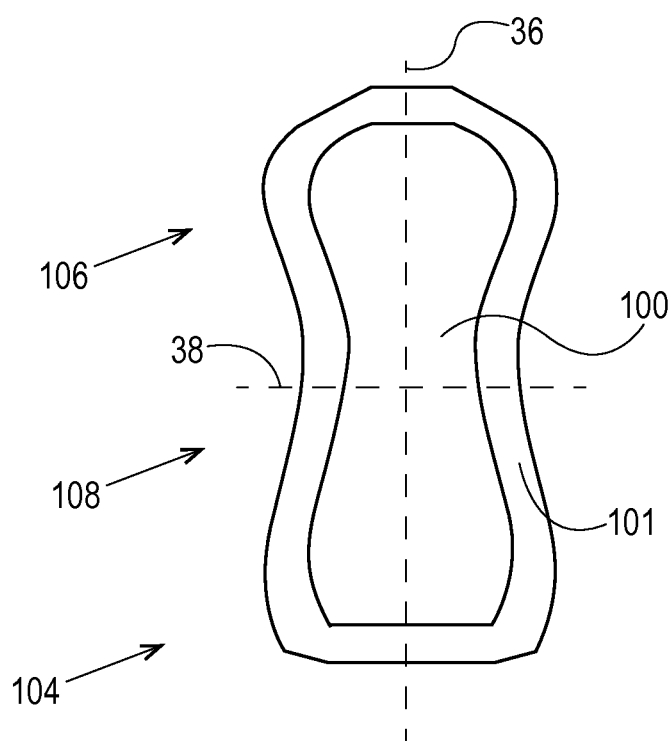
Figure 17:
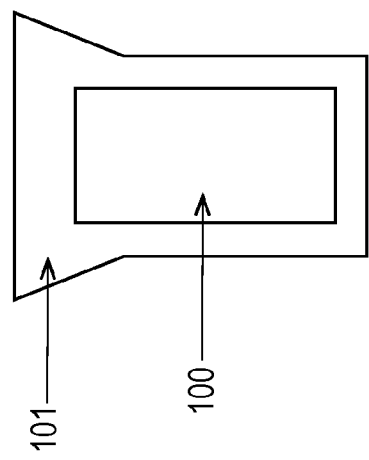
Figure 18:
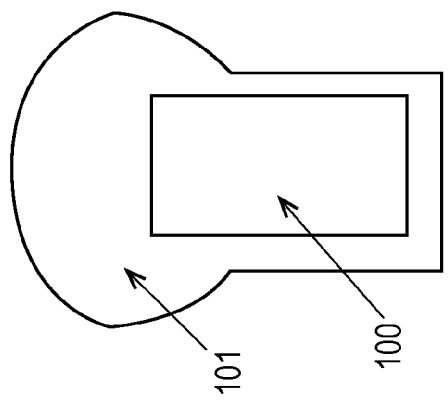
Figure 19:
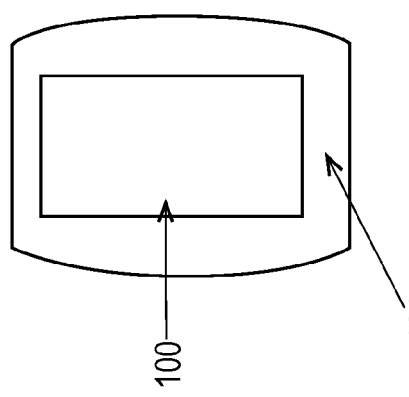
Figure 20:
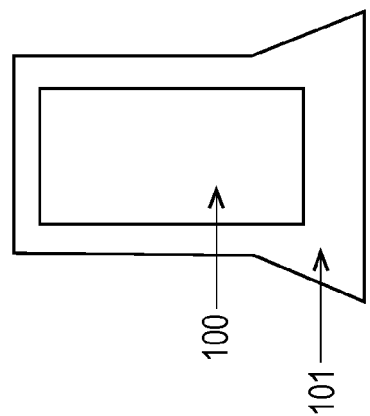
Figure 21:
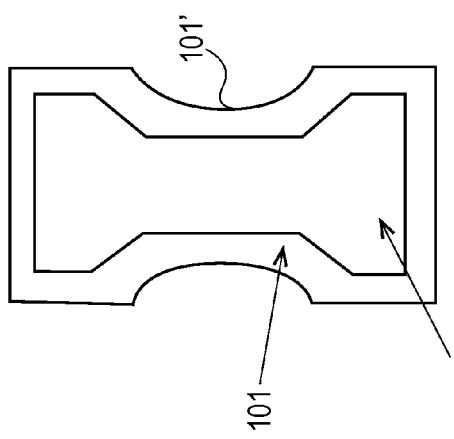

FIGS. 8-34 illustrate various example configurations of raised barriers 101 and absorbent bodies 101 of the present disclosure. Although these examples are illustrated outside of an absorbent article or diaper 10 context for illustration, it will be understood that such configurations would be suitable for use in diapers, sanitary napkins, and/or other absorbent articles. As can be seen from examples illustrated in FIGS. 8-34, the thicknesses and shapes of the raised barriers 101 may vary significantly or slightly. Furthermore, the shapes of the absorbent bodies 100 can vary. Now specific figures will be referenced to illustrate certain additional features of the present disclosure. The front waist region 104, the crotch region 108, and the back waist region 106 are indicated in FIGS. 8-10. The front, crotch, and back waist regions are oriented the same way in FIGS. 11-34, although not specifically indicated on each figure. The front waist regions 104, the crotch regions 108, and the back waist regions 106 of FIGS. 8-34 would be positioned in a front waist region, a crotch region, and a back waist region, respectively, of a diaper, for example diaper 10 of FIG. 7. In each of FIGS. 8-34, the wearer-facing surface is oriented toward the viewer. The longitudinal axis 36 and the lateral axis 38 are indicated on FIGS. 8, 9, and 10 and are in the same orientation for FIGS. 11-34, although not specifically indicated. The longitudinal axis 36 and the lateral axis 38 correspond to the longitudinal axis 36 and the lateral axis 38 of the diaper 10 of FIG. 7, for example.

Figure 23:
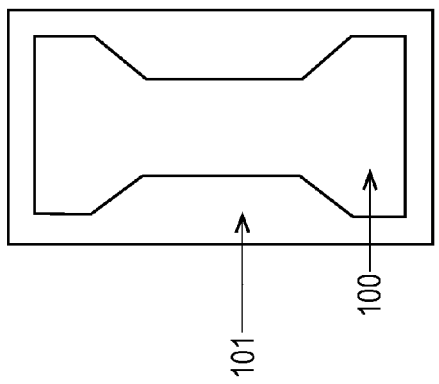
Figure 25:
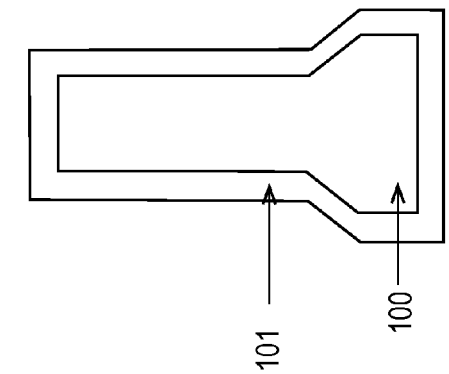

In FIGS. 10-20 and 32-34, the internal barrier area maximum width is the same, or substantially the same, in the front waist region 104 and the back waist region 106. Further, the internal barrier area maximum widths of the front and back waist regions 104 and 106 are the same as the internal barrier area width of the crotch region 108. In FIGS. 8, 9, 21, 22, and 25-30, the internal barrier area maximum width in the front and back waist regions 104 is larger than the internal barrier area width in the crotch region 108. In FIG. 23, the internal barrier area width in the crotch region 108 is the same as, or substantially the same as, the internal barrier area maximum width in the back waist region 106, while in FIG. 24, the internal barrier area width in the crotch region 108 is the same as, or substantially the same as, the internal barrier area maximum width in the front waist region 104. In FIG. 25, the internal barrier area maximum width in the back waist region 106 is larger than the internal barrier area maximum width in the front waist region 104 and larger than the internal barrier area width in the crotch region 108, while in FIG. 29, the internal barrier area maximum width in the front waist region 104 is larger than the internal barrier area maximum width in the back waist region 106 and larger than the internal barrier area width in the crotch region 108. Some of FIGS. 8-34 show raised barriers with a constant thickness, while others of FIG. 8-34 show raised barriers having a varying thickness.

FIG. 13 illustrates a three piece raised barrier. Two similarly, or the same, shaped pieces 101' are positioned at the longitudinal ends of the raised barrier while a third piece 101 of the raised barrier extends between them. This embodiment is provided to show that the raised barrier may be formed of a plurality of components and still form a raised barrier surrounding, at least partially surrounding, or surrounding a portion of, the absorbent body 100.

FIG. 14 illustrates a raised barrier 101 having a diamond shaped outer perimeter. In such an embodiment, the barrier width of the crotch region 108 exceeds the barrier width of the front waist region 104 and the barrier width of the back waist region 106.

Figure 22:
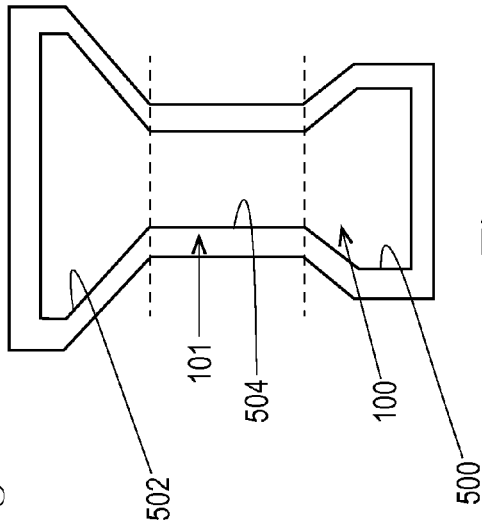
Figure 24:
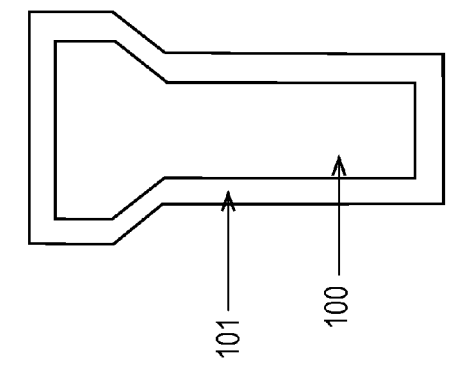

FIG. 22 illustrates a raised barrier 101 with leg openings 101' defined therein.

Figure 29:
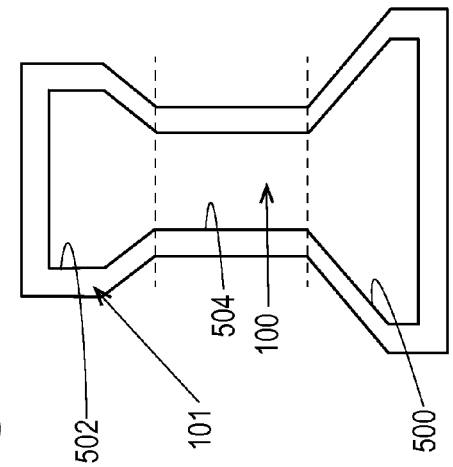

FIGS. 25 and 29 illustrate raised barriers 101 having first internal barrier area shapes 500 in the front waist regions 104, second internal barrier area shapes 502 in the back waist regions 106, and third internal barrier area shapes 504 in the crotch regions 108. In such an embodiment, the first barrier area shapes 500 may be different than the second internal barrier area shapes 502 and the third barrier area shapes 504. The sizes or areas of the various internal barrier area shapes may also be different or the same in various embodiments. In other embodiments, all of the internal barrier area shapes may be the same and may have the same area (see e.g., FIG. 10)

Figure 28:
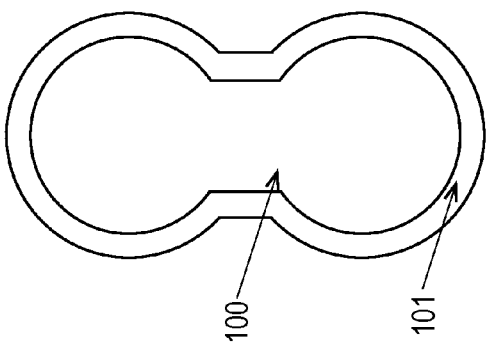
Figure 30:
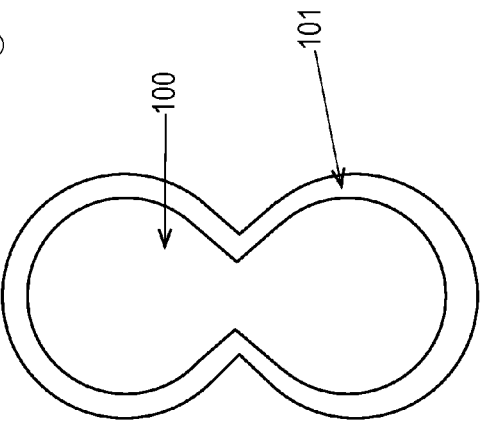
Figure 27:
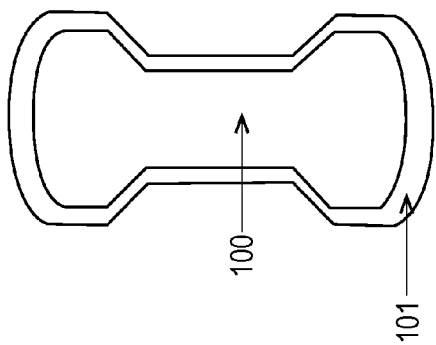
Figure 26:
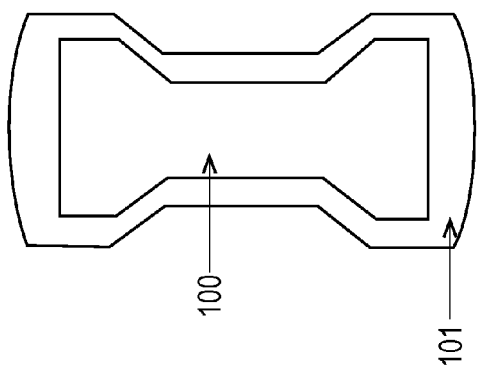
Figure 31:
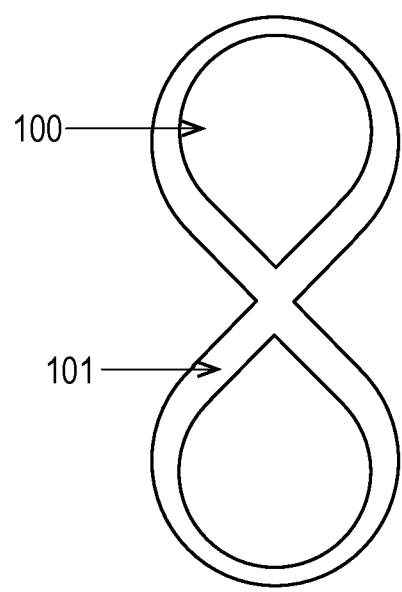

FIGS. 28, 30, and 31 illustrate raised barriers 101 forming a figure eight-like shapes (FIGS. 28 and 30) or figure eight shapes (FIG. 31) and being continuous. The raised barriers 101 comprise at least one arcuate portion.

Figure 34:
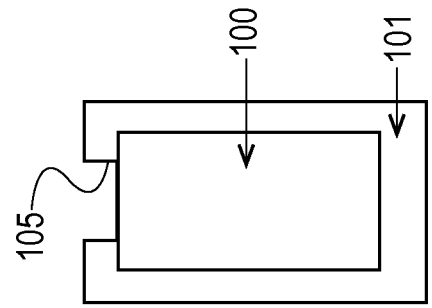
Figure 33:
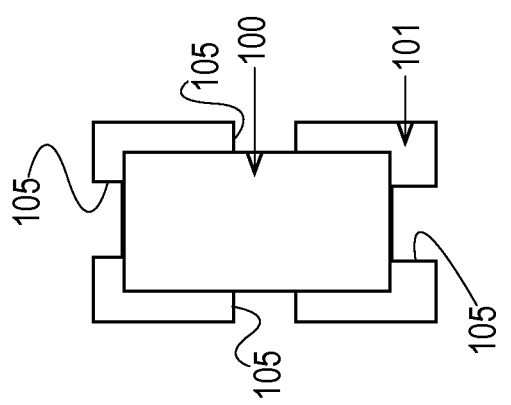
Figure 32:
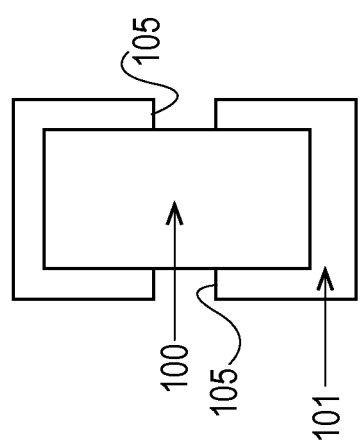
Figure 35:
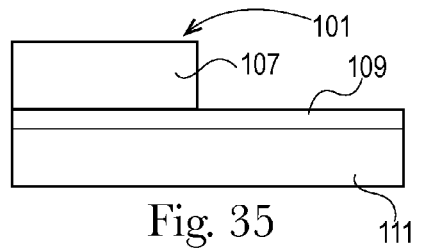
FIGS. 35-46 are example schematic cross-sectional illustrations taken about line X-X of FIG. 8 illustrating various configurations of raised barriers, acquisition layers, and absorbent bodies in accordance with various non-limiting embodiments.
Figure 40:
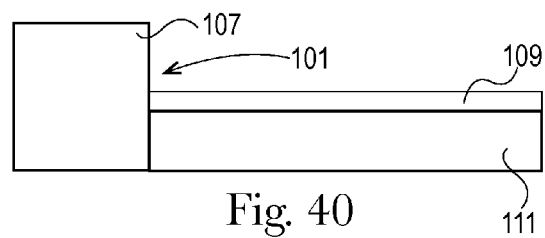
Figure 36:
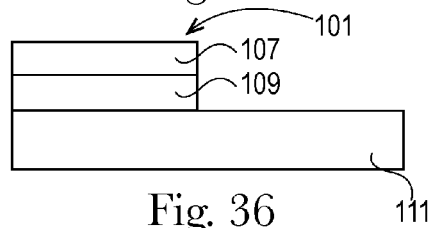
Figure 41:
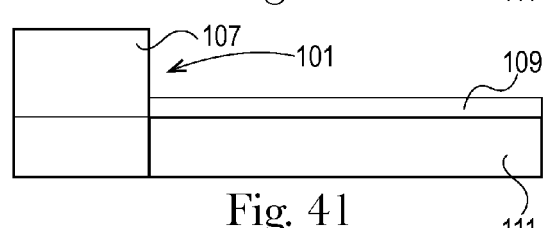
Figure 37:
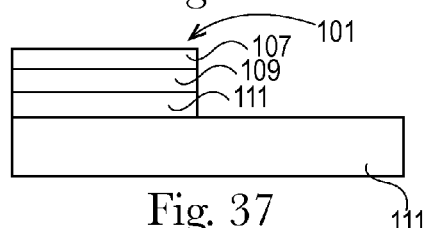
Figure 42:
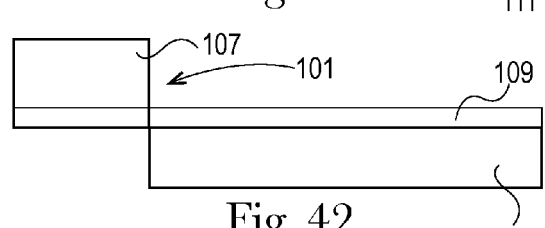
Figure 38:
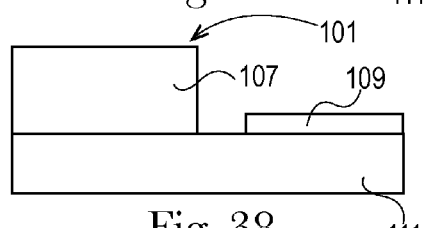
Figure 43:
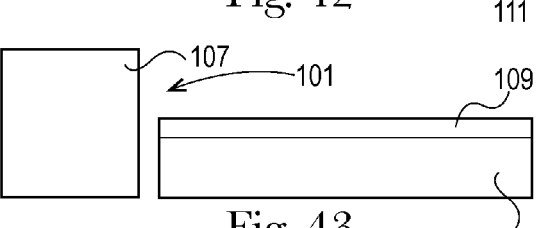
Figure 39:
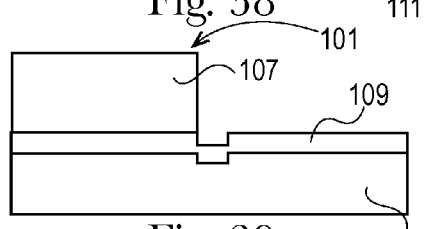
Figure 44:
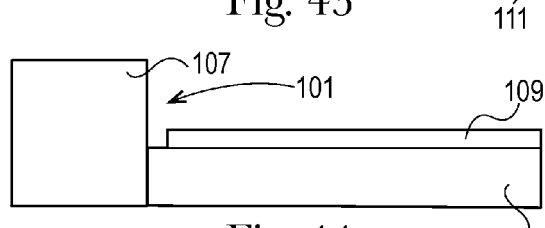
Figure 45:
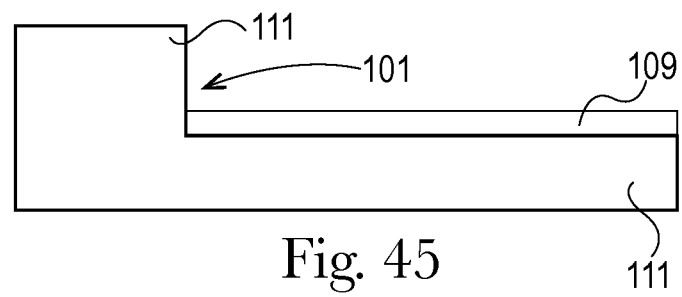
Figure 46:
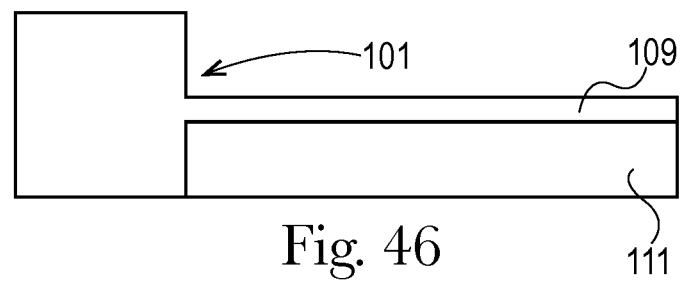

FIGS. 32-34 illustrate raised barriers 101 that are discontinuous, as indicated by gaps 105. The gaps may be formed in the raised barriers in any suitable location.

FIGS. 35-46 illustrate example schematic cross-sectional illustrations taken about line X-X of FIG. 8. The topsheet or backsheet are not shown in these illustrations, nor is any web covering the raised barrier. It will be understood that these components, and other components, may also be present in various configurations. Reference number 107 is used to indicate barrier material of the raised barrier. Reference number 109 is used to indicate one or more acquisition layers. Reference number 111 is used to indicate one or more layers of an absorbent core. In these embodiments, the one or more acquisition layers 109 and the one or more layers of the absorbent core 111 form the absorbent body 100. As can be seen in these figures, the raised barrier 101 may be formed at least in part from one or more acquisition layers 109, portions of the absorbent core 111, and/or the barrier material 107. In other embodiments, the raised barrier 101 may only be formed from the barrier material. In any embodiments of the present disclosure, the raised barrier 101 may be formed of one or more barrier materials 107. The acquisition layer(s) 109 and/or the absorbent core 111 may extend under or to the barrier material 107. In other embodiments, a gap may be created between an end edge of an acquisition layer 109 and the barrier material 107 and/or between the absorbent core 109 and the barrier material 107. The gap may be useful in holding liquid or exudates until the absorbent core 109 can absorb it. In one embodiment, referring to FIG. 45, the absorbent core 111 may form the raised barrier 101. In another embodiment, referring to FIG. 46, the acquisition layers 109 may form the raised barrier 101.

In various embodiments, a raised barrier with or without a material (e.g., a soft nonwoven web or the topsheet if the raised barrier is positioned under the topsheet) covering it may extend about 0.2 mm to about 30 mm, about 0.5 mm to about 25 mm, about 1 mm to about 22 mm, about 2 mm to about 20 mm, about 2 mm to about 15 mm, about 5 mm to about 15 mm, about 6 mm to about 15 mm, or at least 5 mm, specifically reciting all 0.1 mm increments within the specified ranges and all ranges formed therein or thereby, from a portion of the wearer-facing surface of the topsheet positioned within the internal barrier area. In various embodiments, the distance that the raised barrier extends from a portion of the topsheet on the wearer-facing surface in the internal barrier area may be constant around the perimeter of the raised barrier or may vary around the perimeter of the raised barrier. In an instance in which the height of the barrier varies, a larger or smaller height may be present in the front waist region or the back waist region that is more particularly suited to retain urine and/or runny BM, for example.

Using a rigid measuring instrument graduated in mm, the height of a particular raised barrier or the heights at various locations of the raised barrier may be determined. To measure the height of the raised barrier at a particular point about its perimeter, the diaper or absorbent article should be positioned on a flat surface in a flat, laid out state (no elastic contraction). An end of the rigid measuring instrument should then be positioned against (but not pressing into) the-wearer facing surface of the topsheet in the internal barrier area. The measuring instrument should extend upwards past the top (further away from the topsheet) of the raised barrier. The measuring instrument should be positioned in a vertical orientation. The measuring instrument should be positioned proximate to, if not touching, the raised barrier to obtain an accurate measurement. The measuring instrument should then be read and the height should be reported to the closest +/−0.5 mm.

The raised barrier may be symmetrical or asymmetrical about the lateral axis 38 in an absorbent article, such as a diaper. The raised barrier may also be symmetrical or asymmetrical about the longitudinal axis 36 in an absorbent article, such as a diaper. In the case of an asymmetrical shaped barrier, the larger portion of the barrier layer may reside in the front waist region or the back waist region to either better protect against leakage or to be optimally designed for differentiated disposable diapers for boys and girls. One function of the raised barrier, regardless of shape, is to provide additional containment or retention for urine and/or runny BM.

Figure 47:
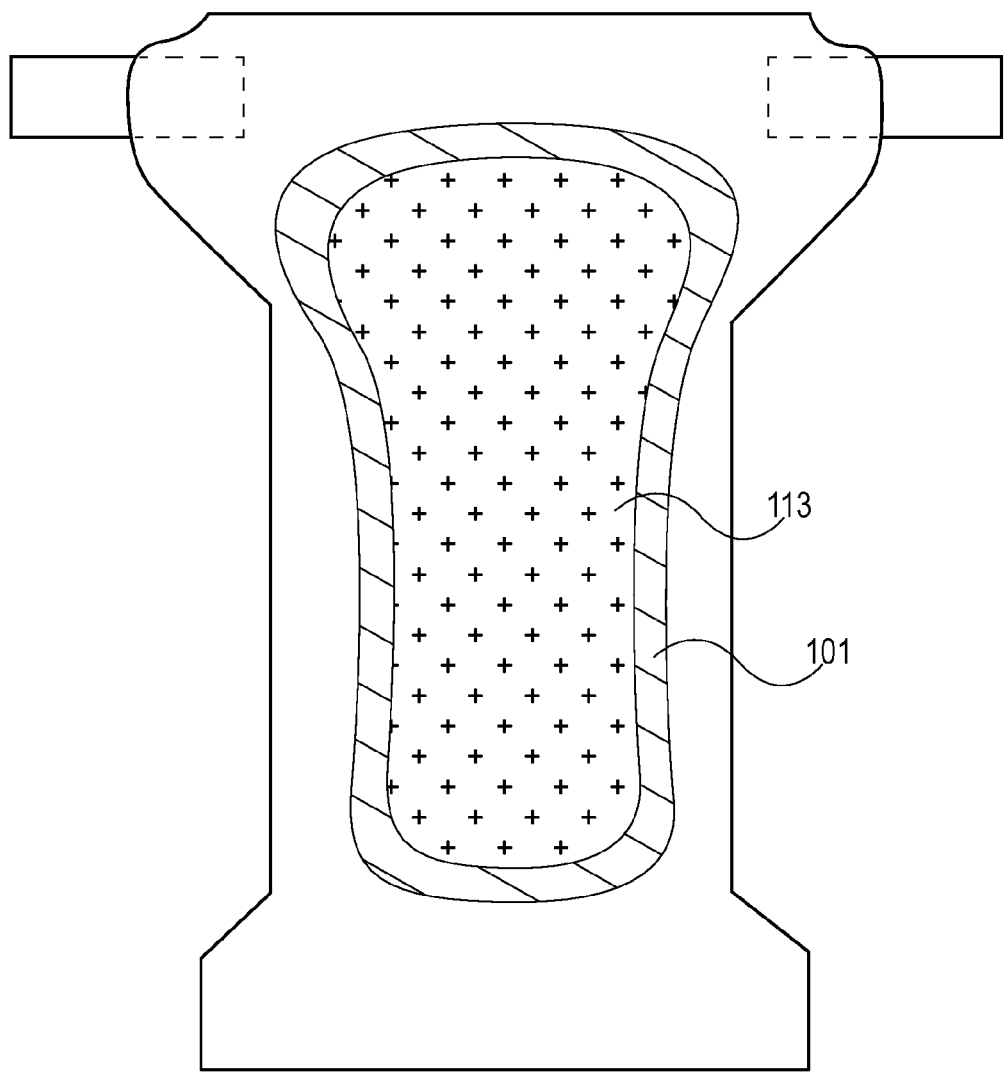
FIG. 47 is a plan view of an example absorbent article shown laid out horizontally in a stretched out, flattened state (stretched out against elastic contraction induced by the presence of elastic members), wearer-facing surface oriented toward the viewer and having a raised barrier in accordance with one non-limiting embodiment.

In an embodiment, the raised barrier and/or the material covering it may have a different feature or property as compared to the topsheet 113 positioned over the absorbent body and within the internal barrier area or to the topsheet positioned outside of the internal barrier area. In one instance, the material covering the raised barrier may be a nonwoven web attached to the topsheet (pocket embodiment discussed above), while in other instances, the topsheet of the absorbent article may be the material covering the raised barrier. Referring to FIG. 47, an absorbent article is illustrated with a raised barrier 101 at least partially surrounding, or fully surrounding a perimeter or portion of an absorbent body 100. As can be seen, the raised barrier 101 has a different feature than the topsheet 113 positioned over the absorbent body within the internal barrier area. Such a distinguishing feature may include a different texture, color, pattern, or combinations thereof, as compared to the absorbent body. Different colors may be light blue and dark blue, or graduations to each, for example. Also, the raised barrier may have a similar feature as compared to the topsheet 113 positioned over absorbent body within the absorbent body. Such a similar feature may include a different texture, color, pattern, aperture pattern, or combinations thereof, as compared to the topsheet positioned over the absorbent body. Including varying or complementary aesthetic features of the raised barrier and the topsheet 113 positioned over the absorbent body may enable the caregiver to more easily align the product to the wearer when applying the product to the wearer. In an embodiment, the topsheet 113 positioned over the absorbent body and/or the topsheet or other material positioned over the raised barrier may be somewhat transparent. In such an embodiment, the material forming the raised barrier may have a different feature than the material forming a wearer-facing surface of absorbent body, for example color.

The top edge of the raised barrier (the portion of the raised barrier most distal from the wearer-facing surface) may be planer with the wearer-facing surface or may be angled with respect to the wearer-facing surface. In various embodiments, a plurality of indentations may be formed in the top edge or other portion of the raised barrier.

In an embodiment, more than one raised barrier may be provided on a single absorbent article for added protection against leakage.

In various embodiments, the raised barriers may be attachable to the topsheet and/or the absorbent article and removable therefrom. In such an embodiment, the raised barriers may be sold with the absorbent articles or sold separately. In such an embodiment, the raised barrier may have a fastener (e.g., hook material, adhesive) on a topsheet engaging surface thereof that may engage the topsheet to removably attach the raised barrier to the topsheet. By allowing the raised barrier to be removable from the topsheet and/or another portion of the absorbent article, a caregiver may decide to use or not use the raised barrier in certain circumstances. For example, the caregiver may decide to only use the raised barrier at night or when the absorbent article will be worn for an extended period of time. In an embodiment, the removable raised barrier may be absorbent or may comprise an absorbent material so that it essentially creates an exudate seal around the internal barrier area and maintains the exudates within the internal barrier area and/or within the absorbent raised barrier.

In any of the embodiments disclosed herein, regardless of whether the raised barrier is removable, the raised barrier may be absorbent or may comprise an absorbent material such that it creates an exudate seal around the internal barrier area. The absorbent raised barrier may have an outer perimeter that comprises an exudate impermeable portion to further create the seal around the internal barrier area. Internal perimeters of the raised barrier may be liquid permeable/liquid absorbent to allow the raised barrier to absorb exudates.

In an embodiment, a sanitary napkin, feminine pad, or adult incontinence product (together referred to below as a "sanitary napkin") may be provided with the raised barriers described herein. The sanitary napkin may comprise a topsheet, a secondary topsheet, and absorbent body or core, a backsheet, and wings.

Figure 48:
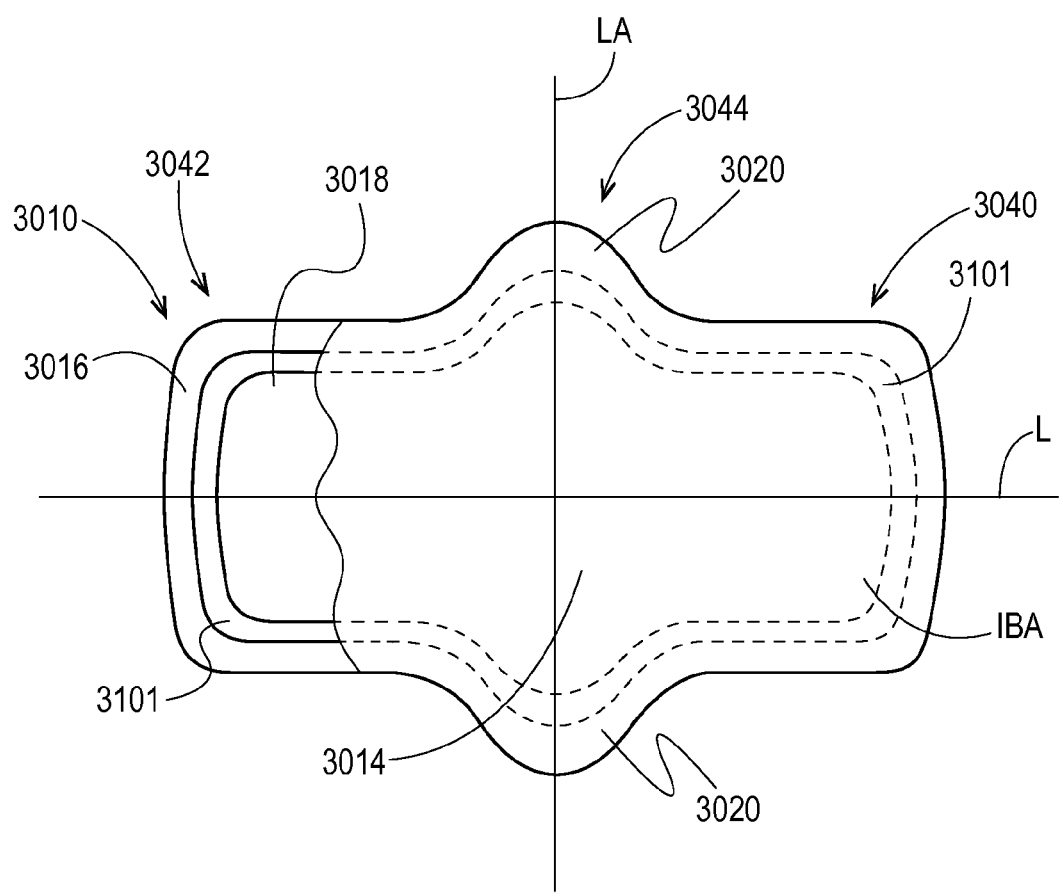
FIG. 48 is a partially cut away plan view of an example sanitary napkin, wearer-facing surface oriented toward the viewer, having a raised barrier in accordance with one non-limiting embodiment.

In an embodiment, referring to FIG. 48, the absorbent article may be a sanitary napkin 3010. The sanitary napkin 3010 may comprise a topsheet 3014, a backsheet 3016, and an absorbent core 3018 positioned intermediate the topsheet 3014 and the backsheet 3016. The sanitary napkin 3010 may also comprise wings 3020 extending outwardly with respect to a longitudinal axis, L, of the sanitary napkin 3010. The sanitary napkin may also have a lateral axis, LA. The wings 3020 may be joined to the topsheet 3014, the backsheet 3016, and/or the absorbent core 3018. The sanitary napkin 3010 may also be provided with additional features commonly found in sanitary napkins as is known in the art.

In an embodiment, still referring to FIG. 48, the sanitary napkin 3010 may comprise the topsheet 3014, optionally a secondary topsheet (not illustrated), the backsheet 3016, and the absorbent core 3018 positioned at least partially intermediate the topsheet 3014 and the backsheet 3016. The sanitary napkin 3010 may comprise one or more raised barriers 3101 optionally positioned outboard of the absorbent core 3018 and surrounding, or at least partially surrounding, the absorbent core 3018. In another embodiment, the raised barrier 3101 may be positioned inboard of the perimeter of the absorbent core 3018 or may be positioned on or proximate to the perimeter of the absorbent core 3018. The raised barrier 3101 may be positioned intermediate the topsheet 3014 and the backsheet 3014, may be positioned under the topsheet 3014, or may be positioned on top of the topsheet 3014 (the same as or similar to that described above). The raised barrier 3101 defines an internal barrier area, IBA, in the sanitary napkin 3010. A portion of the topsheet 3014 positioned over the raised barrier 3101 or a top portion of the raised barrier 3101 extends at least 2 mm and less than 20 mm above a portion of the topsheet 3014 positioned within the internal barrier area, IBA. The portion of the topsheet 3014 positioned over the raised barrier 3101 may have a different texture, color, and/or pattern than the remainder of the topsheet 3014. Alternatively, the raised barrier 3101 may have a different texture, color, and/or pattern than the remainder of the topsheet 3014. The sanitary napkin 3010 has a lateral axis, LA, a front region 3040 on a first side of the lateral axis, LA, a back region 3042 on a second side of the lateral axis, LA, and a central region 3044 positioned intermediate the front region 3040 and the back region 3042. The raised barrier 3101 may extend into the front region 3040, the back region 3042, and/or the central region 3044. In other embodiments, the raised barrier 3101 may only extend into one or more of the regions. The front region 3040 has a first internal barrier area shape and/or size. The central region 3044 has a second internal barrier area shape and/or size. The back region 3042 has a third internal barrier area shape and/or size. The first internal barrier area shape and/or size and the third internal barrier area shape and/or size may be the same or different and both may be the same or different as the second internal barrier area shape and/or size. The raised barrier 3101 may have any suitable features and configurations as the raised barriers described herein, such as raised barriers 101.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a topsheet;
a backsheet;
an absorbent body positioned at least partially intermediate the topsheet and the backsheet;
a pair of elasticized leg cuffs each comprising a free end positioned distal from the topsheet;
a raised barrier positioned outboard of the absorbent body and at least partially surrounding the absorbent body, wherein the raised barrier is positioned intermediate the topsheet and the backsheet, wherein the raised barrier is positioned at least partially intermediate the pair of the elasticized leg cuffs, wherein the raised barrier defines an internal barrier area in the absorbent article, and wherein the raised barrier extends at least 1 mm and less than 15 mm above a portion of the topsheet positioned within the internal barrier area;
a lateral axis;
a front waist region on a first side of the lateral axis;
a back waist region on a second side of the lateral axis; and
a crotch region positioned intermediate the front waist region and the back waist region, wherein the raised barrier extends into the front waist region, the back waist region, and the crotch region;
the front waist region having an internal barrier area maximum width measured parallel to the lateral axis and intermediate two most distal, laterally inboard, opposing portions of the raised barrier in the front waist region;
the crotch region having an internal barrier area width measured on the lateral axis and intermediate two laterally inboard opposing portions of the raised barrier in the crotch region; and
the back waist region having an internal barrier area maximum width measured parallel to the lateral axis and intermediate two most distal, laterally inboard, opposing portions of the raised barrier in the back waist region, wherein the internal barrier area maximum width of the back waist region is larger than the internal barrier area width of the crotch region;
wherein the raised barrier comprises a portion that is free of an elastic and extends continuously across a longitudinal axis of the absorbent article.

2. The absorbent article of claim 1, wherein the raised barrier is continuous and comprises a compressible, resilient material and an arcuate portion.

3. The absorbent article of claim 1, wherein the raised barrier is discontinuous.

4. The absorbent article of claim 1, wherein a ratio of the back waist region internal barrier area maximum width to the crotch region internal barrier area width is about 2.4 to about 1.1.

5. The absorbent article of claim 1, wherein the raised barrier is a separate structure from the absorbent body.

6. The absorbent article of claim 1, wherein the internal barrier area maximum width of the back waist region is larger than the internal barrier area maximum width of the front waist region.

7. The absorbent article of claim 1, wherein a portion of the topsheet positioned within the internal barrier area has a different texture, color, pattern, aperture pattern, or combinations thereof as compared to the remainder of the topsheet.

8. An absorbent article comprising:
a topsheet;
a backsheet;
an absorbent body positioned at least partially intermediate the topsheet and the backsheet;
a pair of elasticized leg cuffs each comprising a free end positioned distal from the topsheet;
a raised barrier positioned outboard of the absorbent body and at least partially surrounding the absorbent body, wherein the raised barrier is positioned intermediate the topsheet and the backsheet, wherein the raised barrier is positioned at least partially intermediate the pair of the elasticized leg cuffs, wherein the raised barrier defines an internal barrier area in the absorbent article, and wherein the raised barrier extends at least 1 mm and less than 15 mm above a portion of the topsheet positioned within the internal barrier area;
a lateral axis;
a front waist region on a first side of the lateral axis;
a back waist region on a second side of the lateral axis; and
a crotch region positioned intermediate the front waist region and the back waist region, wherein the raised barrier extends into the front waist region, the back waist region, and the crotch region;
the front waist region having a barrier maximum width measured parallel to the lateral axis and intermediate two most distal, laterally outboard, opposing portions of the raised barrier in the front waist region;
the crotch region having a barrier width measured on the lateral axis and intermediate two laterally outboard opposing portions of the raised barrier in the crotch region; and
the back waist region having a barrier maximum width measured parallel to the lateral axis and intermediate two most distal, laterally outboard, opposing portions of the raised barrier in the back waist region, wherein the barrier maximum width of the back waist region is larger than the barrier width of the crotch region;
wherein the raised barrier comprises:
an absorbent material;
an outer perimeter that comprises an exudate seal; and
an inner perimeter that is liquid permeable or liquid absorbent; and
wherein the raised barrier crosses a longitudinal axis of the absorbent article.

9. The absorbent article of claim 8, wherein a portion of the topsheet positioned over the raised barrier has a different texture, color, pattern, or combinations thereof, as compared to the remainder of the topsheet.

10. The absorbent article of claim 8, wherein the raised barrier is a separate structure from the absorbent body, and wherein the barrier maximum width of the back waist region is larger than the barrier maximum width of the front waist region.

11. The absorbent article of claim 8, wherein the raised barrier is continuous.

12. The absorbent article of claim 8, wherein a ratio of the back waist region barrier maximum width to the crotch region barrier width is 2.4 to 1.1, and wherein a ratio of the front waist region barrier maximum width to the crotch region barrier width is 2.4 to 1.

13. An absorbent article comprising:
a topsheet;
a backsheet;
an absorbent body positioned at least partially intermediate the topsheet and the backsheet;
a raised barrier positioned outboard of the absorbent body and at least partially surrounding the absorbent body, wherein the raised barrier is positioned intermediate the topsheet and the backsheet, wherein the raised barrier defines an internal barrier area in the absorbent article, wherein a portion of the topsheet positioned over the raised barrier extends at least 1 mm and less than 15 mm above a portion of the topsheet positioned within the internal barrier area, wherein the raised barrier has a thickness in the range of about 2 mm to about 50 mm, and wherein the portion of the topsheet positioned over the raised barrier has a different texture, color, or pattern than the remainder of the topsheet;
a lateral axis;
a longitudinal axis, wherein a first portion of the raised barrier crosses the longitudinal axis at a first location, and wherein the raised barrier crosses the longitudinal axis at a second location;
a front waist region on a first side of the lateral axis;
a back waist region on a second side of the lateral axis; and
a crotch region positioned intermediate the front waist region and the back waist region, wherein the raised barrier extends into the front waist region, the back waist region, and the crotch region;
the front waist region having a first internal barrier area shape;
the crotch region having a second internal barrier area shape; and
the back waist region having a third internal barrier area shape, wherein the third internal barrier area shape is different than the second internal barrier area shape.

14. The absorbent article of claim 13, wherein the absorbent article is a taped diaper comprising elasticized leg cuffs, and wherein the first barrier area shape is different than the third barrier area shape.

15. A sanitary napkin comprising:
a topsheet;
a backsheet;
an absorbent core positioned at least partially intermediate the topsheet and the backsheet;
a raised barrier positioned outboard of the absorbent core and at least partially surrounding the absorbent core, wherein the entire raised barrier is positioned intermediate the topsheet and the backsheet, wherein the raised barrier defines an internal barrier area in the sanitary napkin, wherein a portion of the topsheet positioned over the raised barrier extends at least 1 mm and less than 15 mm above a portion of the topsheet positioned within the internal barrier area, wherein the raised barrier has a thickness in the range of about 2 mm to about 50 mm, and wherein the portion of the topsheet positioned over the raised barrier has a different texture, color, or pattern than the remainder of the topsheet;
a lateral axis;
a front region on a first side of the lateral axis;
a back region on a second side of the lateral axis; and
a central region positioned intermediate the front region and the back region, wherein the raised barrier extends into the front region, the back region, and the central region;
the front region having a first internal barrier area shape;
the central region having a second internal barrier area shape; and
the back region having a third internal barrier area shape, wherein the third internal barrier area shape is different than the second internal barrier area shape.

16. The absorbent article of claim 1, wherein the raised barrier fully surrounds the absorbent body.

17. The absorbent article of claim 15, comprising a longitudinal axis, wherein the raised barrier crosses the longitudinal axis at a first location and at a second location.

18. The absorbent article of claim 1, wherein the raised barrier comprises a second portion that extends across the longitudinal axis of the absorbent article at a different location than the portion.

19. The absorbent article of claim 8, wherein the raised barrier crosses the longitudinal axis at a first location and at a second, different location.

* * * * *